United States Patent
Shadduck

(10) Patent No.: US 7,674,259 B2
(45) Date of Patent: *Mar. 9, 2010

(54) MEDICAL INSTRUMENTS AND TECHNIQUES FOR THERMALLY-MEDIATED THERAPIES

(75) Inventor: John H. Shadduck, Tiburon, CA (US)

(73) Assignee: Tsunami MedTech, Berkeley, CA (US)

( * ) Notice: Subject to any disclaimer, the term of this patent is extended or adjusted under 35 U.S.C. 154(b) by 388 days.

This patent is subject to a terminal disclaimer.

(21) Appl. No.: 10/681,625

(22) Filed: Oct. 7, 2003

(65) Prior Publication Data

US 2004/0068306 A1 Apr. 8, 2004

Related U.S. Application Data

(63) Continuation-in-part of application No. 10/017,582, filed on Dec. 7, 2001, now Pat. No. 6,669,694.

(60) Provisional application No. 60/416,622, filed on Oct. 7, 2002, provisional application No. 60/254,487, filed on Dec. 9, 2000.

(51) Int. Cl.
  *A61B 18/18* (2006.01)
(52) U.S. Cl. .......................... 606/41; 606/27
(58) Field of Classification Search ............. 606/27–31, 606/41, 45–50; 607/101–105
  See application file for complete search history.

(56) References Cited

U.S. PATENT DOCUMENTS

| 4,682,596 A | 7/1987 | Bales et al. |
| 4,773,410 A | 9/1988 | Blackmer et al. |
| 5,122,138 A | 6/1992 | Manwaring |
| 5,318,014 A | 6/1994 | Carter |
| 5,462,521 A | 10/1995 | Brucker et al. |
| 5,554,172 A | 9/1996 | Horner et al. |
| 5,562,608 A | 10/1996 | Sekins et al. |
| 5,620,440 A | 4/1997 | Heckele et al. |
| 5,669,907 A | 9/1997 | Platt et al. |
| 5,681,282 A | 10/1997 | Eggers et al. |
| 5,683,366 A | 11/1997 | Eggers et al. |
| 5,697,281 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |

(Continued)

FOREIGN PATENT DOCUMENTS

WO  WO 00/11927  3/2000

(Continued)

OTHER PUBLICATIONS

U.S. Appl. No. 09/181,906, filed Oct. 28, 1998, in the name of Shadduck, Notice of Allowance mailed Dec. 5, 2000.

(Continued)

*Primary Examiner*—Michael Peffley
(74) *Attorney, Agent, or Firm*—Levine Bagade Han LLP

(57) ABSTRACT

A surgical instrument for thermally-mediated therapies in targeted tissue volumes and for causing thermal effects in polymer tissue-contacting members. In one embodiment, the instrument has a working end with an interior chamber that is supplied with a biocompatible liquid. An energy source causes a liquid-to-vapor phase change within the interior of the instrument. The vapor phase media then is ejected from the working surface of the instrument, and a controlled vapor-to-liquid phase change in an interface with tissue applies thermal energy substantially equal to the heat of vaporization to ablate tissue. The vapor-to-liquid phase transitions, or internal energy releases, can be provided about thin-film flexible structures for engaging body lumens and cavities. An exemplary embodiment can be used for shrinking, sealing, welding or creating lesions in tissue—while causing limited collateral thermal damage and while totally eliminating electrical current flow in the engaged tissue.

13 Claims, 26 Drawing Sheets

U.S. PATENT DOCUMENTS

| | | | |
|---|---|---|---|
| 5,800,482 A | 9/1998 | Pomeranz et al. | |
| 5,810,764 A | 9/1998 | Eggers et al. | |
| 5,843,019 A | 12/1998 | Eggers et al. | |
| 5,891,095 A | 4/1999 | Eggers et al. | |
| 5,891,134 A * | 4/1999 | Goble et al. | 606/27 |
| 5,913,856 A | 6/1999 | Chia et al. | |
| 5,944,715 A | 8/1999 | Goble et al. | |
| 5,964,752 A * | 10/1999 | Stone | 606/27 |
| 5,989,445 A | 11/1999 | Wise et al. | |
| 6,032,077 A | 2/2000 | Pomeranz | |
| 6,032,674 A | 3/2000 | Eggers et al. | |
| 6,047,700 A | 4/2000 | Eggers et al. | |
| 6,053,909 A | 4/2000 | Shadduck | |
| 6,066,134 A | 5/2000 | Eggers et al. | |
| 6,139,571 A | 10/2000 | Fuller et al. | |
| 6,149,620 A | 11/2000 | Eggers et al. | |
| 6,159,194 A | 12/2000 | Eggers et al. | |
| 6,168,594 B1 | 1/2001 | LaFontaine et al. | |
| 6,190,381 B1 | 2/2001 | Olsen et al. | |
| 6,210,404 B1 | 4/2001 | Shadduck | |
| 6,224,592 B1 | 5/2001 | Eggers et al. | |
| 6,235,020 B1 | 5/2001 | Cheng et al. | |
| 6,261,286 B1 | 7/2001 | Goble et al. | |
| 6,264,650 B1 | 7/2001 | Hovda et al. | |
| 6,264,651 B1 | 7/2001 | Underwood et al. | |
| 6,277,112 B1 | 8/2001 | Underwood et al. | |
| 6,283,961 B1 | 9/2001 | Underwood et al. | |
| 6,312,408 B1 | 11/2001 | Eggers et al. | |
| 6,355,032 B1 | 3/2002 | Hovda et al. | |
| 6,391,025 B1 | 5/2002 | Weinstein et al. | |
| 6,394,949 B1 | 5/2002 | Crowley et al. | |
| 6,416,508 B1 | 7/2002 | Eggers et al. | |
| 6,461,350 B1 | 10/2002 | Underwood et al. | |
| 6,464,695 B2 | 10/2002 | Hovda et al. | |
| 6,468,274 B1 | 10/2002 | Alleyne et al. | |
| 6,482,201 B1 | 11/2002 | Olsen et al. | |
| 6,488,673 B1 | 12/2002 | Laufer et al. | |
| 6,508,816 B2 * | 1/2003 | Shadduck | 606/34 |
| 6,540,741 B1 | 4/2003 | Underwood et al. | |
| 6,575,968 B1 | 6/2003 | Eggers et al. | |
| 6,582,423 B1 | 6/2003 | Thapliyal et al. | |
| 6,610,043 B1 | 8/2003 | Ingenito | |
| 6,620,155 B2 | 9/2003 | Underwood et al. | |
| 6,632,193 B1 | 10/2003 | Davison et al. | |
| 6,632,220 B1 | 10/2003 | Eggers et al. | |
| 6,659,106 B1 | 12/2003 | Hovda et al. | |
| 6,669,694 B2 * | 12/2003 | Shadduck | 606/41 |
| 6,682,520 B2 | 1/2004 | Ingenito | |
| 6,712,811 B2 | 3/2004 | Underwood et al. | |
| 6,719,738 B2 | 4/2004 | Mehier | |
| 6,719,754 B2 | 4/2004 | Underwood et al. | |
| 6,726,684 B1 | 4/2004 | Woloszko et al. | |
| 6,746,447 B2 | 6/2004 | Davison et al. | |
| 6,766,202 B2 | 7/2004 | Underwood et al. | |
| 6,770,071 B2 | 8/2004 | Woloszko et al. | |
| 6,772,012 B2 | 8/2004 | Ricart et al. | |
| 6,832,996 B2 | 12/2004 | Woloszko et al. | |
| 6,837,884 B2 | 1/2005 | Woloszko | |
| 6,837,888 B2 | 1/2005 | Ciarrocca et al. | |
| 6,911,028 B2 * | 6/2005 | Shadduck | 606/41 |
| 6,929,640 B1 | 8/2005 | Underwood et al. | |
| 6,986,769 B2 | 1/2006 | Nelson et al. | |
| 7,083,612 B2 | 8/2006 | Littrup et al. | |
| 7,235,070 B2 | 6/2007 | Vanney | |
| 7,335,195 B2 | 2/2008 | Mehier | |
| 2001/0020167 A1 | 9/2001 | Woloszko et al. | |
| 2001/0029370 A1 | 10/2001 | Hovda et al. | |
| 2002/0095152 A1 | 7/2002 | Ciarrocca et al. | |
| 2002/0177846 A1 | 11/2002 | Mulier et al. | |
| 2002/0193789 A1 | 12/2002 | Underwood et al. | |
| 2003/0028189 A1 | 2/2003 | Woloszko et al. | |
| 2003/0040742 A1 | 2/2003 | Underwood et al. | |
| 2003/0097126 A1 | 5/2003 | Woloszko et al. | |
| 2003/0130655 A1 | 7/2003 | Woloszko et al. | |
| 2003/0130738 A1 | 7/2003 | Hovda et al. | |
| 2003/0158545 A1 | 8/2003 | Hovda et al. | |
| 2003/0163178 A1 | 8/2003 | Davison et al. | |
| 2003/0212395 A1 | 11/2003 | Woloszko et al. | |
| 2004/0024398 A1 | 2/2004 | Hovda et al. | |
| 2004/0024399 A1 | 2/2004 | Sharps et al. | |
| 2004/0049180 A1 | 3/2004 | Sharps et al. | |
| 2004/0054366 A1 | 3/2004 | Davison et al. | |
| 2004/0068306 A1 | 4/2004 | Shadduck | |
| 2004/0087937 A1 | 5/2004 | Eggers et al. | |
| 2004/0116922 A1 | 6/2004 | Hovda et al. | |
| 2004/0199226 A1 | 10/2004 | Shadduck | |
| 2004/0254532 A1 | 12/2004 | Mehier | |
| 2005/0004634 A1 | 1/2005 | Ricart et al. | |
| 2005/0010205 A1 | 1/2005 | Hovda et al. | |
| 2005/0119650 A1 | 6/2005 | Sanders et al. | |
| 2005/0171582 A1 | 8/2005 | Matlock | |
| 2005/0187543 A1 | 8/2005 | Underwood et al. | |
| 2006/0135955 A1 | 6/2006 | Shadduck | |
| 2006/0161233 A1 | 7/2006 | Barry et al. | |
| 2006/0224154 A1 | 10/2006 | Shadduck et al. | |
| 2008/0103566 A1 | 5/2008 | Mehier | |
| 2008/0110457 A1 | 5/2008 | Barry et al. | |
| 2008/0114297 A1 | 5/2008 | Barry et al. | |
| 2009/0149846 A1 | 6/2009 | Hoey et al. | |

FOREIGN PATENT DOCUMENTS

| | | |
|---|---|---|
| WO | WO0029055 A1 | 5/2000 |
| WO | WO 02/069821 | 9/2002 |
| WO | WO03070302 A1 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |

OTHER PUBLICATIONS

U.S. Appl. No. 09/181,906, filed Oct. 28, 1998, in the name of Shadduck, Non-Final Rejection mailed Aug. 17, 2000.

U.S. Appl. No. 09/782,649, filed Feb. 12, 2001, in the name of Shadduck, Notice of Allowance mailed Sep. 13, 2002.

U.S. Appl. No. 10/017,582, filed Dec. 7, 2001, in the name of Shadduck, Notice of Allowance mailed Jul. 23, 2003.

U.S. Appl. No. 10/017,582, filed Dec. 7, 2001, in the name of Shadduck, Non-Final Rejection mailed May 10, 2003.

U.S. Appl. No. 10/346,877, filed Jan. 18, 2003, in the name of Shadduck, Notice of Allowance mailed Apr. 5, 2005.

U.S. Appl. No. 10/346,877, filed Jan. 18, 2003, in the name of Shadduck, Examiner's Amendment mailed Mar. 24, 2005.

U.S. Appl. No. 10/346,877, filed Jan. 18, 2003, in the name of Shadduck, Non-Final Rejection mailed Jan. 31, 2005.

U.S. Appl. No. 11/244,329, filed Jan. 18, 2003, in the name of Shadduck, Notice of Allowance mailed Jun. 1, 2005.

U.S. Appl. No. 11/244,329, filed Jan. 18, 2003, in the name of Shadduck, Examiner's Amendment mailed Apr. 5, 2005.

U.S. Appl. No. 11/244,329, filed Jan. 18, 2003, in the name of Shadduck, Non-Final Rejection mailed Jan. 31, 2005.

U.S. Appl. No. 11/158,930, filed Jun. 22, 2005, in the name of Shadduck, Non-Final Rejection mailed U.S. Appl. No. 11/158,930.

U.S. Appl. No. 10/830,372, filed Apr. 22, 2004, in the name of Shadduck, Notice of Allowance mailed May 14, 2009.

U.S. Appl. No. 10/830,872, filed Apr. 22, 2004, in the name of Shadduck, Final Rejection (PTOL—326) mailed Nov. 7, 2008.

U.S. Appl. No. 10/830,372, filed Apr. 22, 2004, in the name of Shadduck, Examiner Interview Summary (PTOL—413) mailed Apr. 18, 2008.

U.S. Appl. No. 10/830,372, filed Apr. 22, 2004, in the name of Shadduck, Non-Final Rejection mailed Feb. 14, 2008.

Moulding et al., "Preliminary studies for achieving transcervical oviduct occlusion by hot water or low-pressure steam," *Advances in Planned Parenthood*, vol. 12, No. 2; pp. 79-85, 1977.

U.S. Appl. No. 09/181,906, filed Oct. 28, 1998, in the name of Shadduck, Non-Final Rejection mailed Mar. 15, 2000.

U.S. Appl. No. 09/181,906, filed Oct. 28, 1998, in the name of Shadduck, Notice of Allowance mailed Sep. 26, 2000.

U.S. Appl. No. 09/281,493, filed Mar. 30, 1999 in the name of Shadduck, entitled "Ionothermal system and technique for dermal treatments".

U.S. Appl. No. 09/557,931, filed Apr. 22, 2000 in the name of Shadduck, entitled "Ionothermal delivery system and technique for medical procedures".

U.S. Appl. No. 09/580,767, filed May 30, 2000 in the name of Shadduck, entitled "Microjoule electrical discharge catheter for thrombolysis in stroke patients".

U.S. Appl. No. 09/782,649, filed Feb. 12, 2001, in the name of Shadduck, Notice of Allowance mailed Sep. 9, 2002.

U.S. Appl. No. 10/017,582, filed Dec. 7, 2001, in the name of Shadduck, Non-Final Rejection mailed Dec. 10, 2002.

U.S. Appl. No. 10/017,582, filed Dec. 7, 2001, in the name of Shadduck, Non-Final Rejection mailed Jul. 17, 2003.

U.S. Appl. No. 10/346,877, filed Jan. 18, 2003, in the name of Shadduck, Examiner's Amendment mailed Mar. 7, 2005.

U.S. Appl. No. 10/346,877, filed Jan. 18, 2003, in the name of Shadduck, Non-Final Rejection mailed Sep. 30, 2004.

U.S. Appl. No. 10/346,877, filed Jan. 18, 2003, in the name of Shadduck, Notice of Allowance mailed Mar. 7, 2005.

U.S. Appl. No. 11/244,329, filed Jan. 18, 2003, in the name of Shadduck, Non-Final Rejection mailed Jun. 19, 2009.

U.S. Appl. No. 12/465,927, filed May 14, 2009, in the name of Shadduck, entitled "Thermotherapy device".

* cited by examiner

MEDICAL INSTRUMENTS AND TECHNIQUES FOR THERMALLY-MEDIATED THERAPIES

CROSS-REFERENCE TO RELATED APPLICATIONS

This application claims benefit of Provisional U.S. Patent Application Ser. No. 60/416,622 filed Oct. 7, 2002. This application also is a continuation-in-part of U.S. patent application Ser. No. 10/017,582 filed Dec. 7, 2001, now U.S. Pat. No. 6,669,694 which claims benefit of Provisional Patent Application Ser. No. 60/254,487 filed Dec. 9, 2000. All of the above applications are incorporated herein by this reference, together with the specifications of all other commonly-invented applications cited therein.

FIELD OF THE INVENTION

This invention relates to surgical instruments for thermally-mediated treatments of tissue, and more particularly relates to a system for shrinking, sealing, welding or creating lesions in tissue by means of injection of a thermal energy laden vapor media into a body structure wherein the vapor-to-liquid phase change of the media applies energy to the tissue.

BACKGROUND OF THE INVENTION

Various types of radiofrequency (Rf) and laser surgical instruments have been developed for delivering thermal energy to tissue, for example to cause hemostasis, to weld tissue or to cause a thermoplastic remodeling of tissue. While such prior art forms of energy delivery work well for some applications, Rf and laser energy typically cannot cause highly "controlled" and "localized" thermal effects that are desirable in microsurgeries or other precision surgeries. In general, the non-linear or non-uniform characteristics of tissue affect both laser and Rf energy distributions in tissue. The objective of sealing or welding tissue requires means for elevating the tissue temperature uniformly throughout a targeted site.

What is needed is an instrument and technique (i) that can controllably deliver thermal energy to non-uniform tissue volumes; (i) that can shrink, seal, weld or create lesions in selected tissue volumes without desiccation or charring of adjacent tissues; (iii); and (iv) that does not cause stray electrical current flow in tissue.

SUMMARY OF THE INVENTION

The present invention is adapted to provide improved methods of controlled thermal energy delivery to localized tissue volumes, for example for sealing, welding or thermoplastic remodeling of tissue. Of particular interest, the method causes thermal effects in targeted tissue without the use of Rf current flow through the patient's body.

In general, the thermally-mediated treatment method comprises causing a vapor-to-liquid phase state change in a selected media at a targeted tissue site thereby applying thermal energy substantially equal to the heat of vaporization of the selected media to said tissue site. The thermally-mediated therapy can be delivered to tissue by such vapor-to-liquid phase transitions, or "internal energy" releases, about the working surfaces of several types of instruments for endoluminal treatments or for soft tissue thermotherapies. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of internal energies in an introduced media-tissue interaction solves many of the vexing problems associated with energy-tissue interactions in Rf, laser and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (P$\Delta$D) into a resulting vapor phase (see FIG. 1A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy within a targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller—since energy application from the source to the selected media (Rf, laser, microwave etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate—and optionally for controlling propagation velocity of the vapor phase media from the working end surface of the instrument. In use, the method of the invention comprises the controlled deposition of a large amount of energy—the heat of vaporization as in FIG. 1A—when the vapor-to-liquid phase transition is controlled at the vapor media-tissue interface. The vapor-to-liquid phase transition deposits about 580 cal/gram within the targeted tissue site to perform the thermal ablation.

This new ablation modality can utilize specialized instrument working ends for several cardiovascular therapies or soft tissue ablation treatments for tissue sealing, tissue shrinkage, tissue ablation, creation of lesions or volumetric removal of tissue. In general, the instrument and method of the invention advantageously cause thermal ablations rapidly and efficiently compared to conventional Rf energy delivery.

The instrument and method of the invention generate vapor phase media that is controllable as to volume and ejection pressure to provide a not-to-exceed temperature level that prevents desiccation, eschar, smoke and tissue sticking;

The instrument and method of the invention cause an energy-tissue interaction that is imageable with intraoperative ultrasound or MRI;

The instrument and method of the invention advantageously cause thermal effects in tissue that do not rely applying an electrical field across the tissue to be treated; and The instrument and method of the invention advantageously creates thermal effects in a targeted tissue volume with substantially controlled lateral margins between the treated tissue and untreated tissue.

Additional advantages of the invention will be apparent from the following description, the accompanying drawings and the appended claims.

DETAILED DESCRIPTION OF THE INVENTION

Figure 1A:
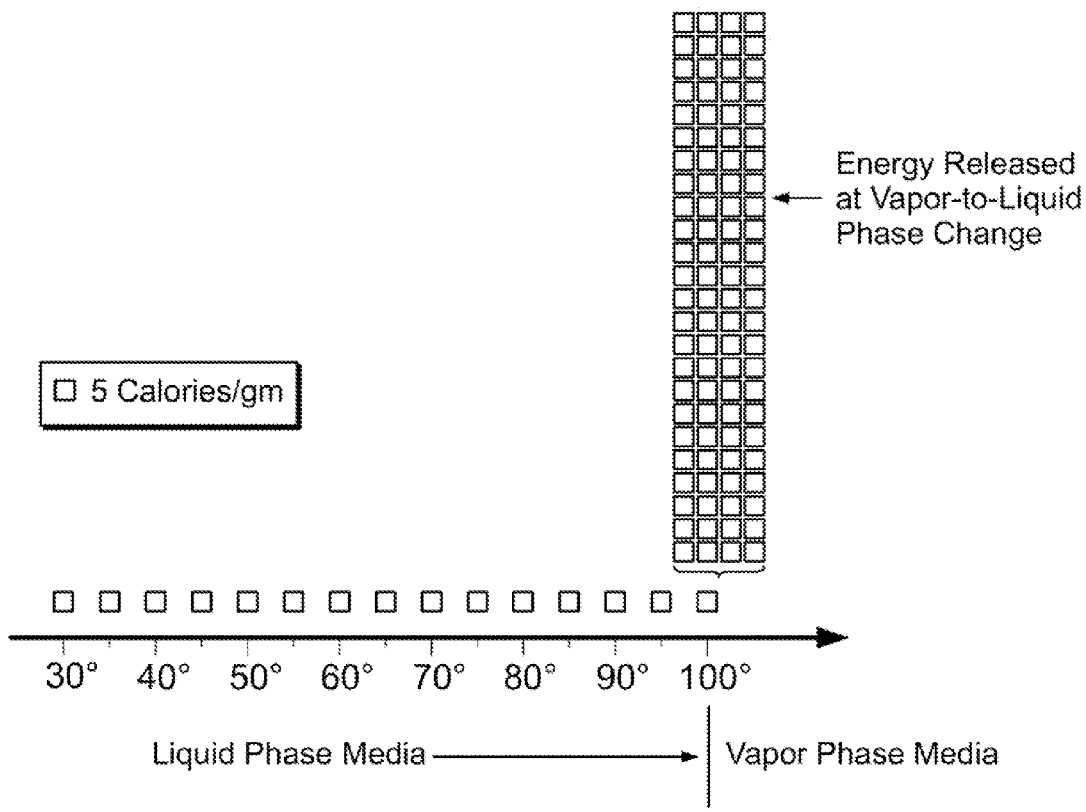
FIG. 1A is a graphical depiction of the quantity of energy needed to achieve the heat of vaporization of water.
Figure 1B:
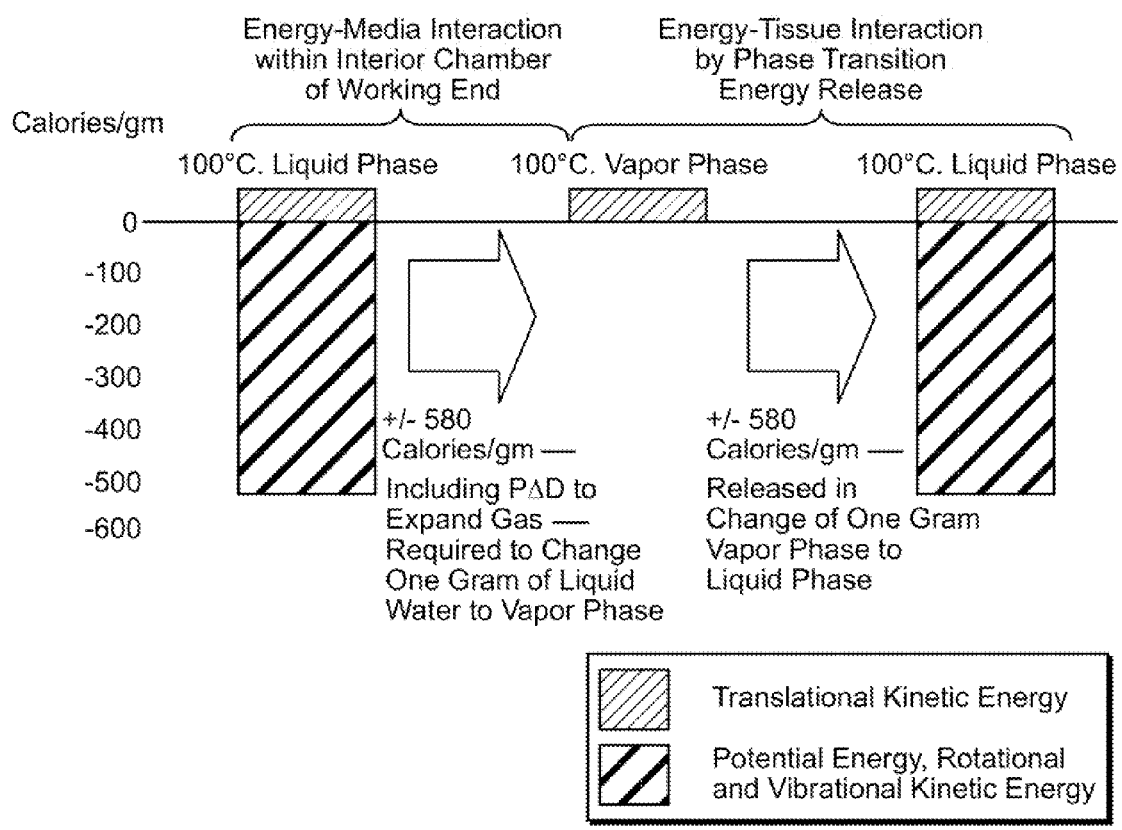
FIG. 1B is a diagram of phase change energy release that underlies one method of the invention.
Figure 2A:
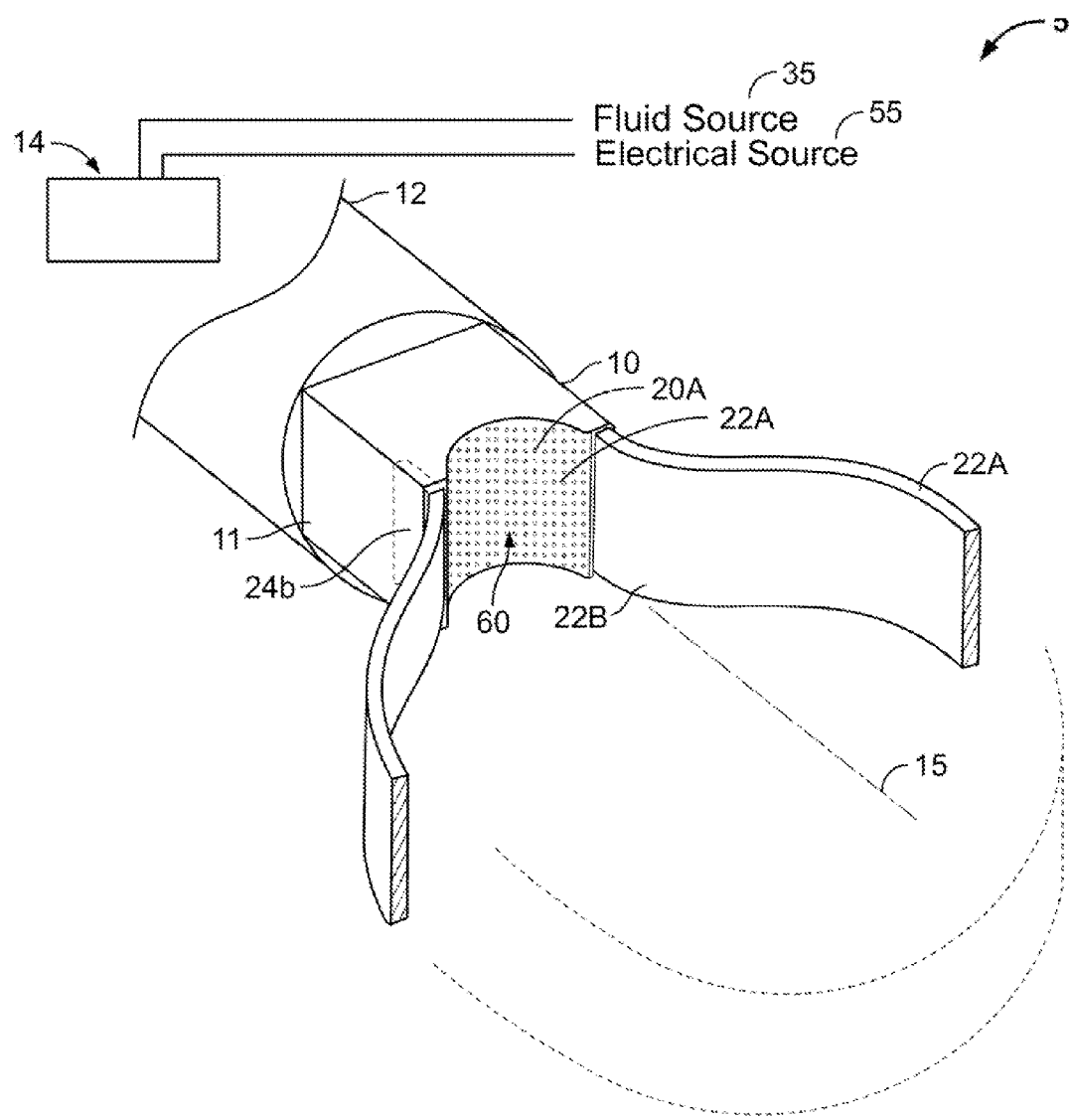
FIG. 2A is a perspective view of the working end of an exemplary Type "A" probe of the present invention with an openable-closeable tissue engaging structure in a first open position.
Figure 2B:
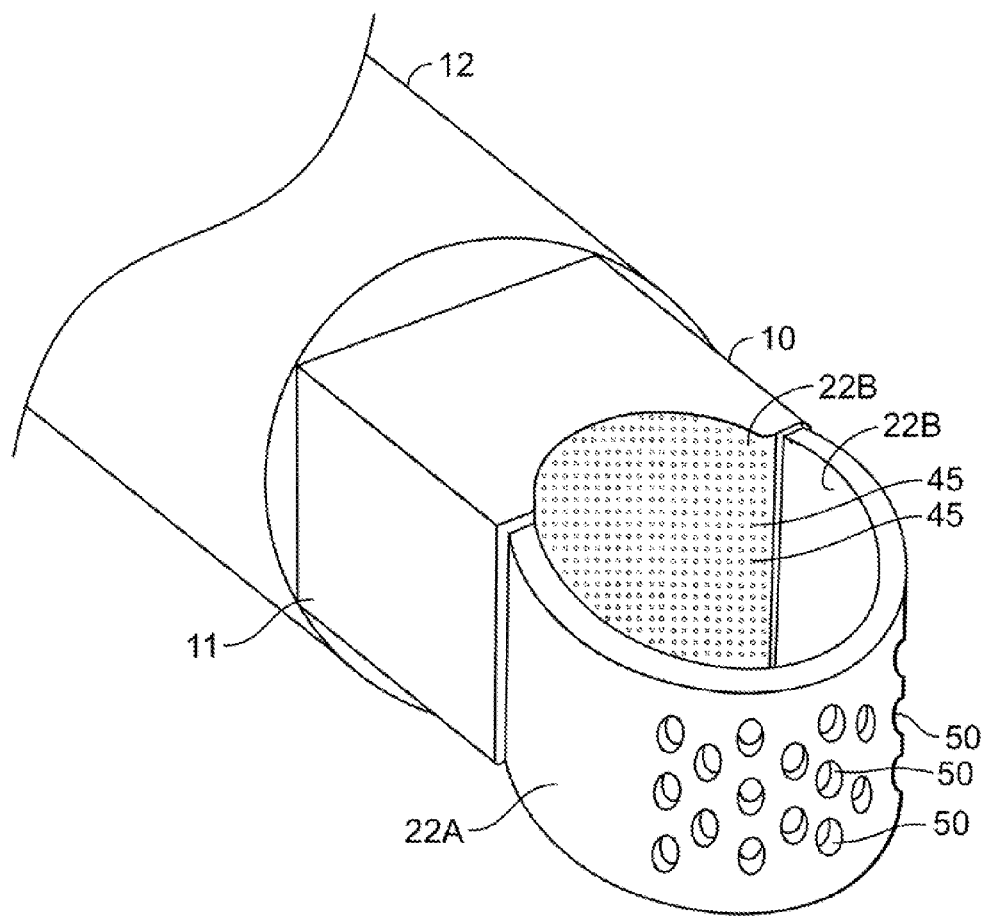
FIG. 2B is a perspective view similar to FIG. 2A probe of the present invention in a second closed position.
Figure 3:
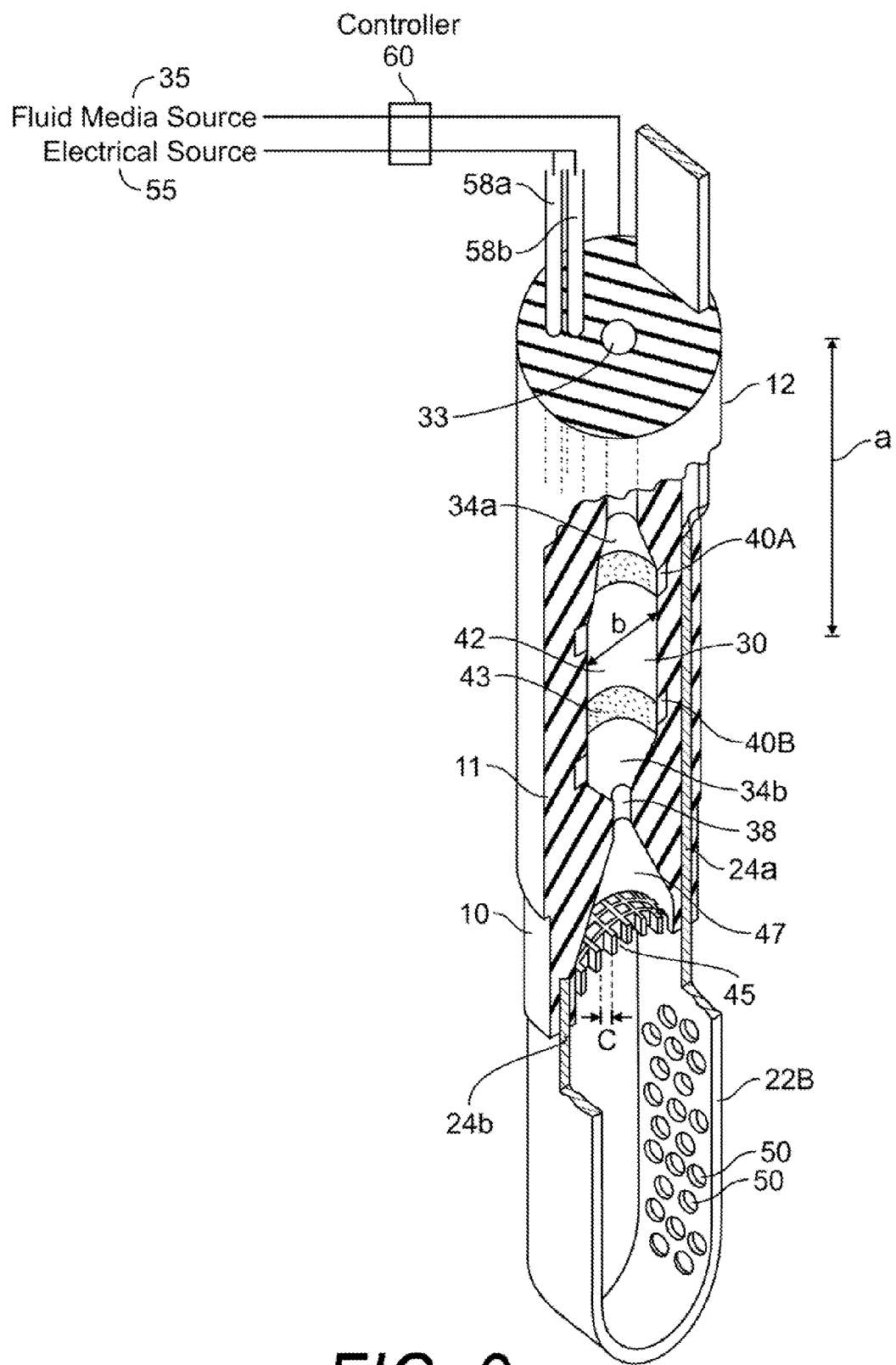
FIG. 3 is a cut-away view of the working end of FIGS. 2A-2B.

1. Type "A" Thermotherapy Instrument. Referring to FIGS. 2A, 2B and 3, the working end 10 of a Type "A" system 5 of the present invention is shown that is adapted for endoscopic procedures in which a tissue volume T targeted for treatment (a thermoplasty) can be captured by a loop structure. The working end 10 comprises a body 11 of insulator material (see FIG. 3) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the working end 10 may be coupled to a rigid shaft member having a suitable 1 mm to 5 mm or larger diameter to cooperate with a trocar sleeve for use in endoscopic or microsurgical procedures. A proximal handle portion 14 of the instrument indicated by the block diagram of FIG. A carries the various actuator mechanisms known in the art for actuating components of the instrument.

In FIGS. 2A, 2B and 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B shows the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which may be a syringe, an elevated remote fluid sac that relies on gravity, or any suitable pump-type pressure means known in the art. The fluid delivery lumen 33 transitions to chamber 30 at proximal end portion 34a thereof. The distal end portion 34b of chamber 30 has a reduced cross-section to (optionally) function as a jet or nozzle indicated at 38.

Of particular interest, still referring to FIG. 3, paired electrode elements 40A and 40B with exposed surfaces and that are spaced apart in surface 42 of the interior fluid confinement chamber 30. In this exemplary embodiment, the electrode elements 40A and 40B comprise circumferential exposed surfaces of a conductive material positioned at opposing proximal and distal ends of interior chamber 30. It should be appreciated that the method of the invention of may utilize any suitable configuration of spaced apart electrodes (e.g., spaces apart helical electrode elements or porous electrodes) about at least one confinement chamber 30 or lumen portion. Alternatively, each electrode can be a singular projecting element that projects into the chamber. The exemplary embodiment of FIG. 3 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 µm) for miniaturized instruments to a larger dimension (e.g., 5.0 mm) for larger instruments for causing the thermally induced fluid-to-gas transformation required to enable the novel phase change energy-tissue interaction of the invention. The electrodes are of any suitable material such as aluminum, stainless steel, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2B and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 4) and as will be described in greater detail below.

FIGS. 2A and 3 show that first tissue-engaging surface 20A defines an open structure of at least one aperture or passageway indicated at 45 that allows vapor pass therethrough. The apertures 45 may have any cross-sectional shape and linear or angular route through surface 20A with a sectional dimension C in this embodiment ranging upwards from micron dimensions (e.g., 0.5 µm) to about 2.0 mm in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to electrical generator 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. The sensor is coupled to controller 60 by a lead (not shown) and can be used to modulate or terminate power delivery as will be described next in the method of the invention.

Figure 4:
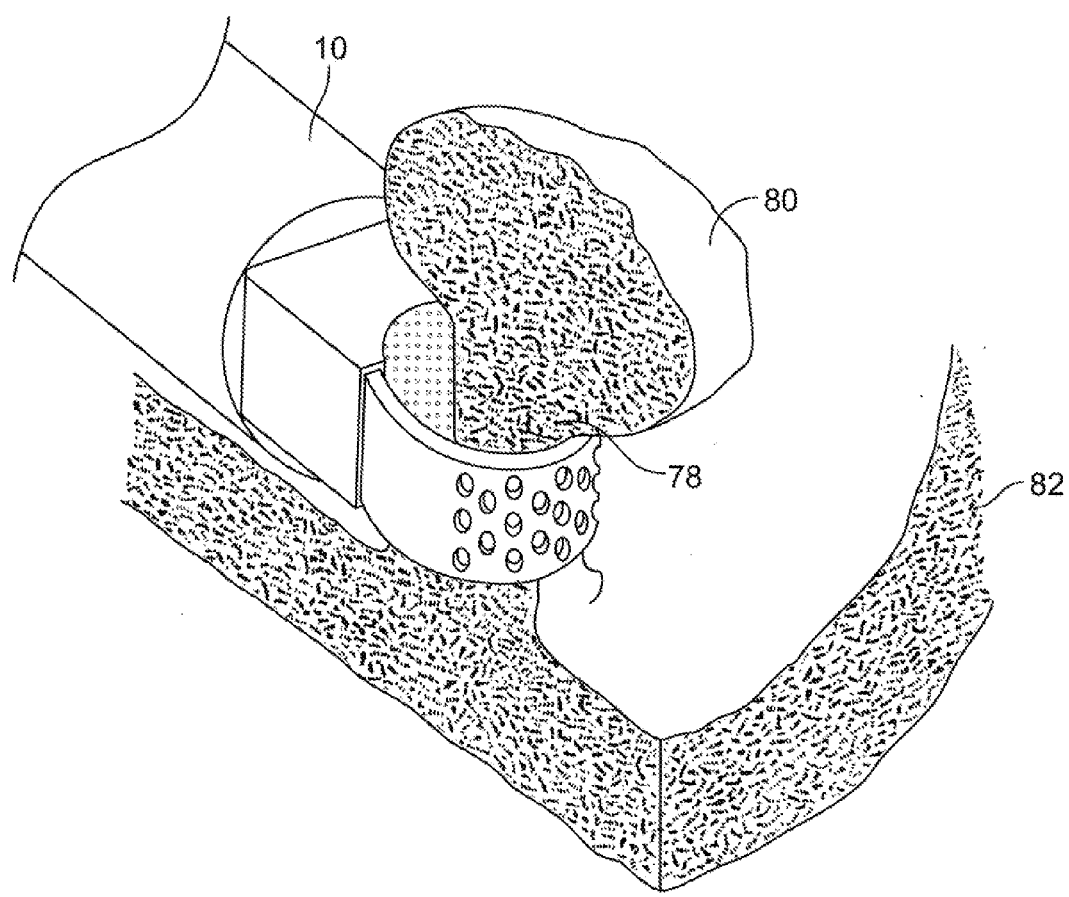
FIG. 4 is a perspective view of the working end of FIG. 3 capturing an exemplary tissue volume.

Operation and use of the working end of FIGS. 2A, 2B and 3 in performing a method of treating tissue can be briefly described as follows, for example in an endoscopic polyp removal procedure. As can be understood from FIG. 4, the working end 10 is carried by an elongate catheter-type member 12 that is introduced through a working channel 70 of an endoscope 72 to a working space. In this case, the tissue T targeted for sealing is a medial portion 78 of a polyp 80 in a colon 82. It can be easily understood that the slidable movement of the loop member 22B can capture the polyp 80 in the device as shown in FIG. 4 after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Figure 5:
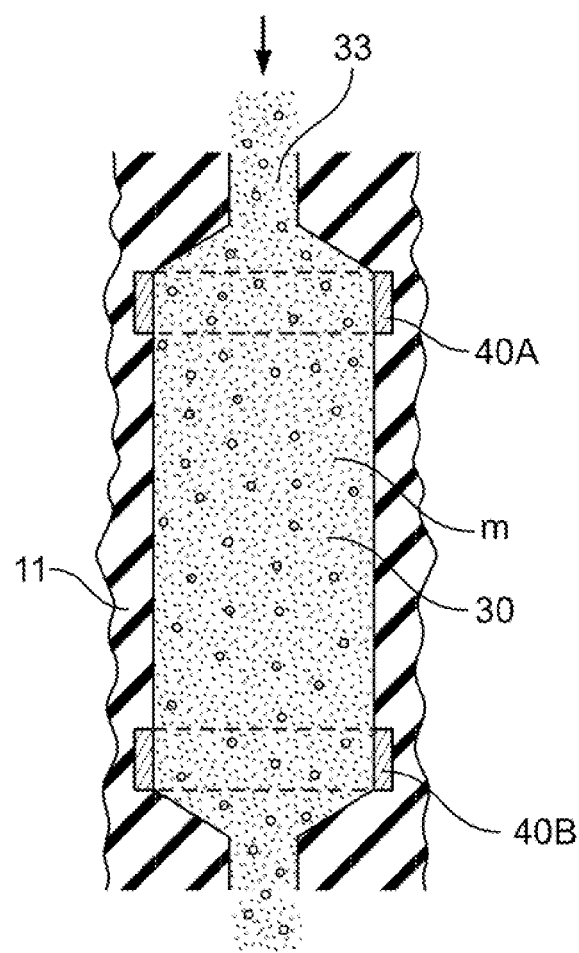
FIGS. 5-6 are sectional schematic views of working end of FIG. 3 depicting, in sequence, the steps of a method of the present invention to seal or weld a targeted tissue volume, FIG. 5 illustrating the pressurized delivery of a liquid media to an interior channel, and FIG. 6 depicting an electrical discharge that causes a liquid-to-gas phase change as well as the ejection of the vapor media into the targeted tissue to cause a thermal weld.
Figure 5:
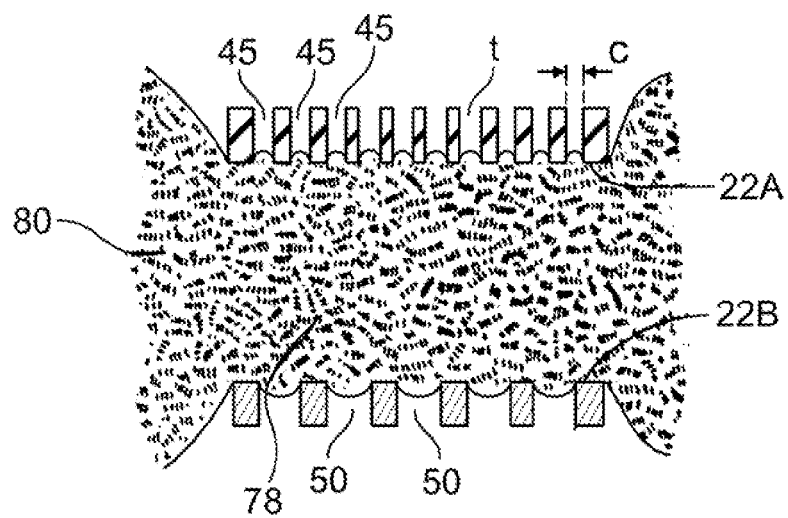
Figure 6:
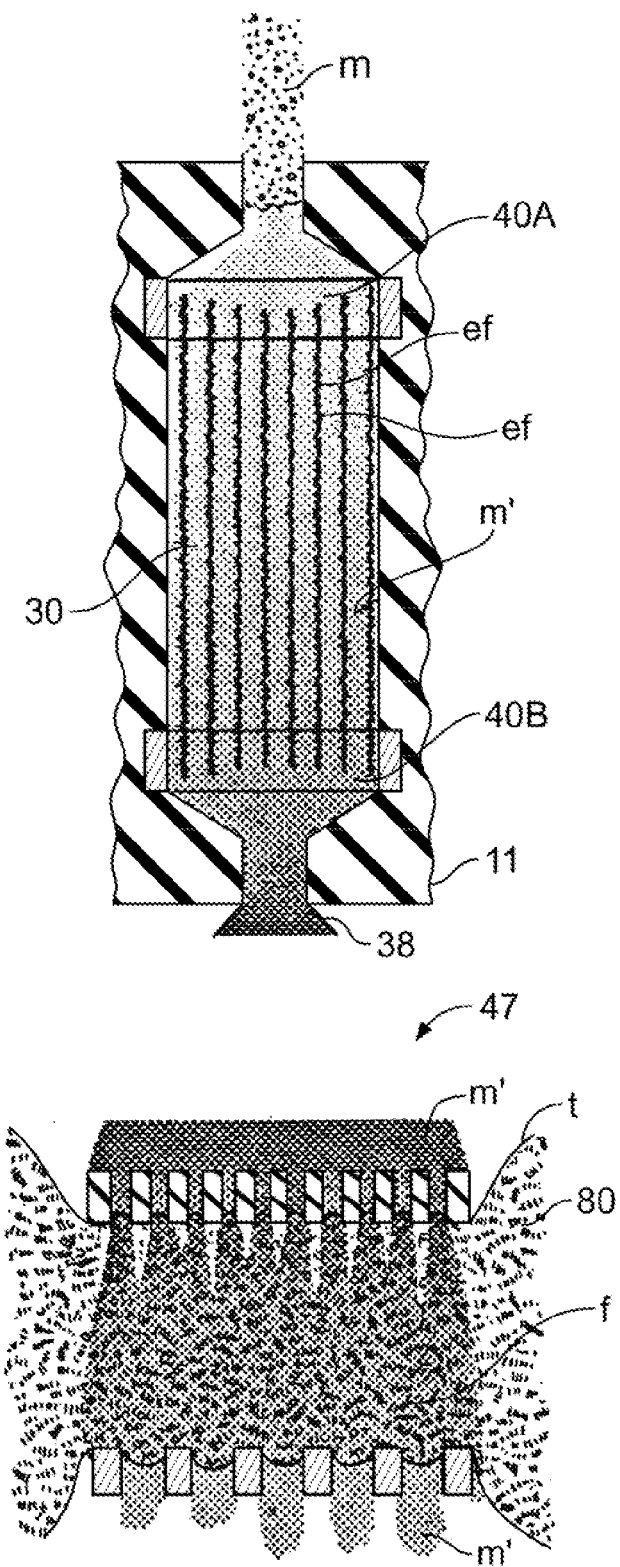

Now turning to FIGS. 5 and 6, two sequential schematic views of the working end engaging tissue T are provided to illustrate the energy-tissue interaction caused by the method of the invention. FIG. 5 depicts an initial step of the method wherein the operator sends a signal to the controller 60 to delivery fluid media M (e.g., saline solution or sterile water) through lumen 33 into chamber 30. FIG. 6 depicts the next step of the method wherein the controller delivers an intense discharge of electrical energy to the paired electrode elements 40A and 40B within chamber 30 indicated by electric arc or electric field EF. The electrical discharge provides energy exceeding the heat of vaporization of the contained fluid volume. The explosive vaporization of fluid media M (of FIG. 5) into a vapor or gas media is indicated at M' in FIG. 6. The greatly increased volume of gas media M' results in the gas being ejected from chamber 30 at high velocity through apertures 45 of surface 20A into the targeted tissue T. The liquid to gas conversion caused by the electrical discharge also heats the gas media M' to about 100° C. to deliver thermal effects into tissue T, or even through the targeted tissue T, as indicated graphically by the shaded regions of gas flow in FIG. 6. The fluid source and its pressure or pump mechanism can provide any desired level of vapor ejection pressure. Depending on the character of the introduced liquid media, the media is altered from a first lesser temperature to a second greater temperature in the range of 100° C. or higher depending on pressure. The ejection of vapor media M' will uniformly elevate the temperature of the engaged tissue to the desired range of about 65° C. to 100° C. very rapidly to cause hydrothermal denaturation of proteins in the tissue, and to cause optimal fluid intermixing of tissue constituents that will result in an effective seal. In effect, the vapor-to-liquid phase transition of the ejected media M' will deposit heat equal to the heat of vaporization in the tissue. At the same time, as the heat of vaporization of media M' is absorbed by water in the targeted tissue, the media converts back to a liquid thus hydrating the targeted tissue T. It is believed that such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 100 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue with an intermixed collagenous volume or scar-like tissue.

An optional method of controlling the repetition rate of electrical discharges comprises the measurement of electrical characteristics of media M within the chamber 30 to insure that the chamber is filled with the fluid media at time of the electrical discharge. The electrical measurement then would send a control signal to the controller 60 to cause each electrical discharge. For example, the liquid media M can be provided with selected conductive compositions in solution therein. The controller 60 then can send a weak electrical current between the paired electrodes 40A and 40B and thereafter sense the change in an impedance level between the electrodes as the chamber 30 is filled with fluid to generate the control signal.

Figure 7:
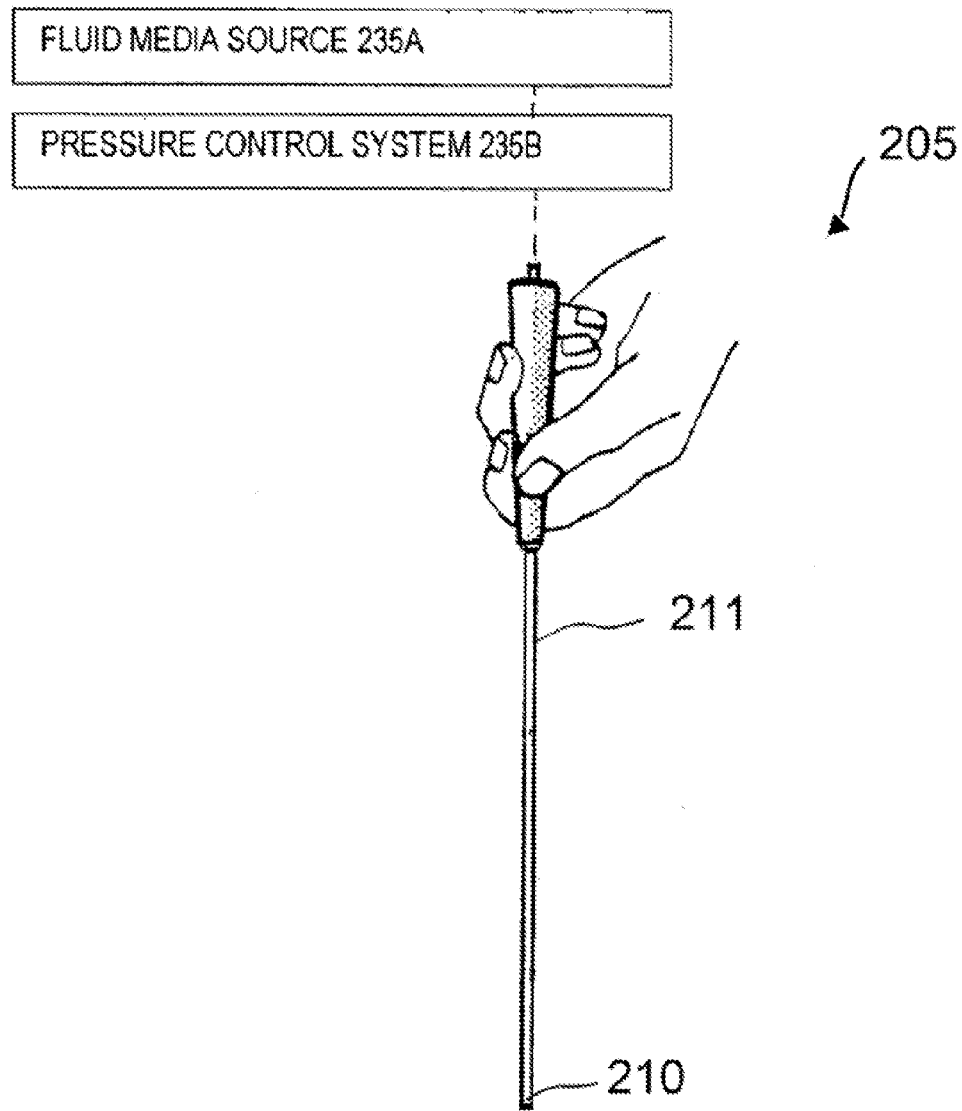
FIG. 7 is a perspective view of an alternative working end of the present invention.

Referring to FIG. 7, a working end 210 of an alternative instrument 205 of the present invention is depicted. The phase transitional energy delivery aspects of the invention are the same as described above. The instrument 205 differs in that it utilizes significantly reduced dimensions (or micronization) of features in the working end 210. More particularly, a fluid media source 235A and pressure control system 235B are adapted to provide pressurized flows of liquid media M through the introducer body 211 and thereafter into microchannel body or structure indicated at 215 (see FIG. 8). The microchannel or microporous body defines therein plurality of small diameter fluid passageways or microchannel portions 216 (collectively). The microchannel body 215 also can be a microporous trabecular material to provide open-cell flow passageways therethrough.

Figure 8:
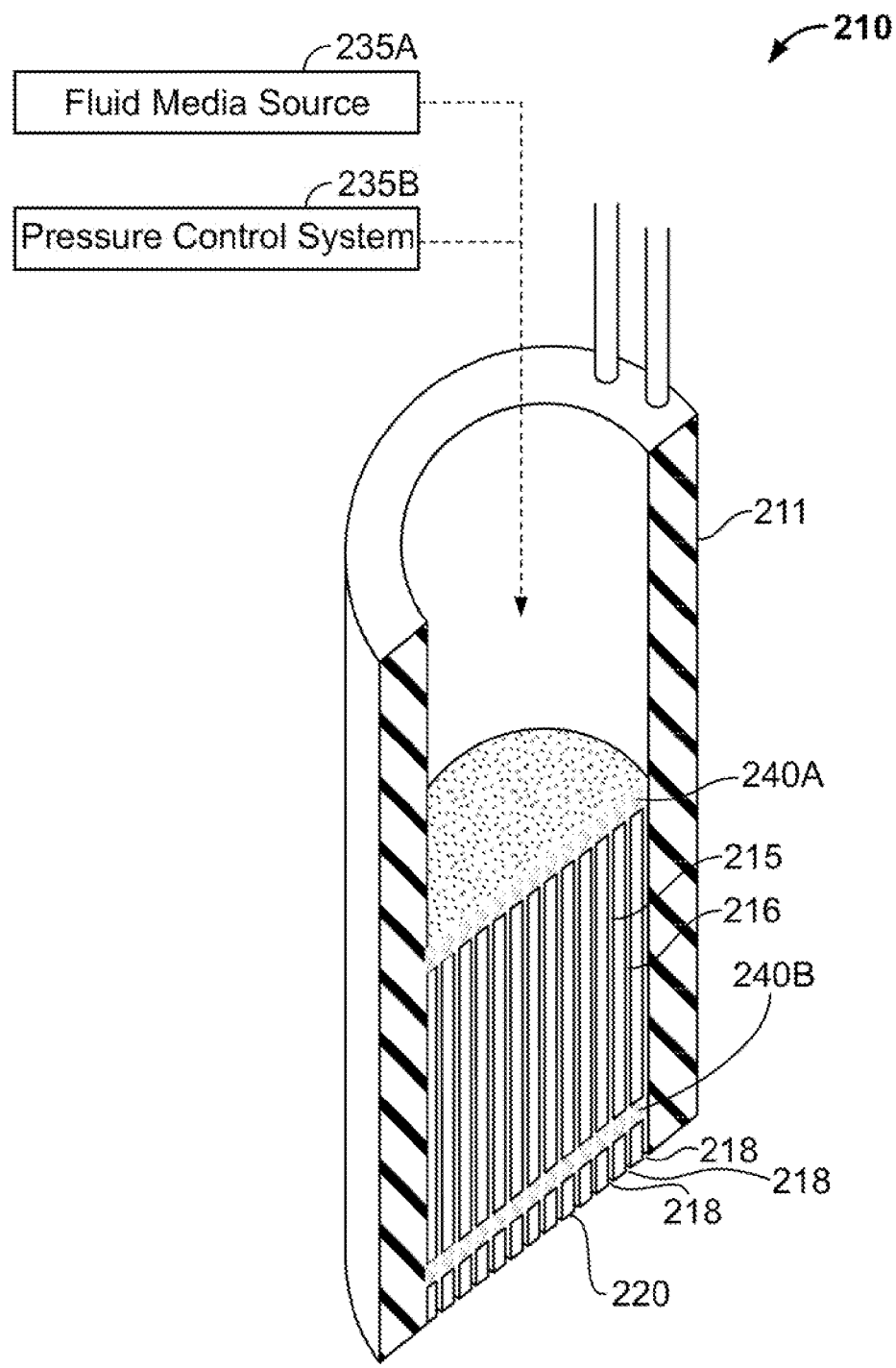
FIG. 8 is a sectional view of the working end of FIG. 7 showing a microchannel structure.
Figure 9:
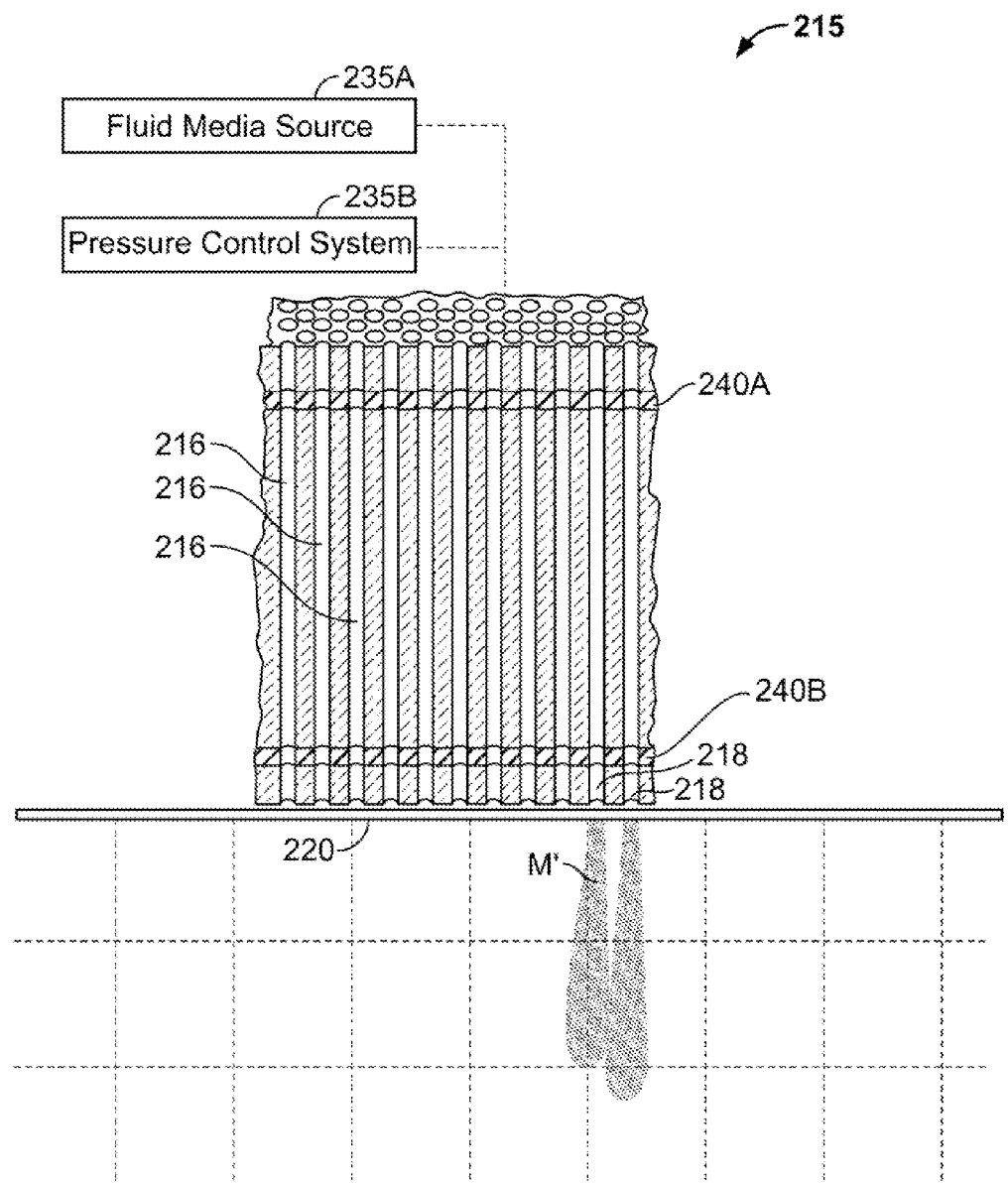
FIG. 9 is a greatly enlarged sectional view of the microchannel structure of FIG. 8 depicting the electrode arrangement carried therein.

In FIG. 8, it can be seen that the microchannel body 215 comprises a structure of an electrically insulative material (or a conductive material with an insulative coating) that defines open flow passageways or channels 216 therethrough that have open terminations or ports 218 in the working surface 220. At an interior of the microchannel body 215, an intermediate region of the open flow channels 216 is exposed to first and second electrode elements 240A and 240B. The electrode elements 240A and 240B can be formed in a plates or layers of channeled material or trabecular material that extends transverse to passageways 216. Thus, the channels are exposed to surfaces of the electrode elements 240A and 240B interior of the working surface 220 that interfaces with the targeted tissue T. As depicted in FIG. 9, electrical energy is applied between the electrodes to cause vaporization of the inflowing liquid media M which is converted to a vapor media M' within the interior of the channels 216 for ejection from the working surface 220 to interact with tissue as described above.

A working end similar to that of FIGS. 7-8 can be used in various thermotherapy procedures. For example, a rigid probe can be used in orthopedic procedures to cause hydrothermal shrinkage of collagen, for example in a spinal disc, or a joint capsule to stabilize the joint (see U.S. patent application Ser. No. 09/049,711 filed Mar. 27, 1998, incorporated herein by this reference). In an arthroscopic procedure, the working end is painted across a targeted tissue site in a joint capsule to shrink tissue. In another procedure, the working end may be stabilized against any collagenous tissue to heat and shrink collagen in a targeted tissue such as a herniated disc. In another procedure, the working end can be painted across the surface of a patient's esophagus to ablate abnormal cells to treat a disorder known as Barrett's esophagus. As described previously, the thermal energy delivery means of the invention preferably uses an electrical energy source and spaced apart electrodes for flash vaporization of a liquid media. It should be appreciated that a resistive element coupled to an electrical source also can be used. For example, a resistive element can fabricated out of any suitable material such a tungsten alloy in a helical, tubular or a microporous form that allows fluid flow therethrough.

Figure 10:
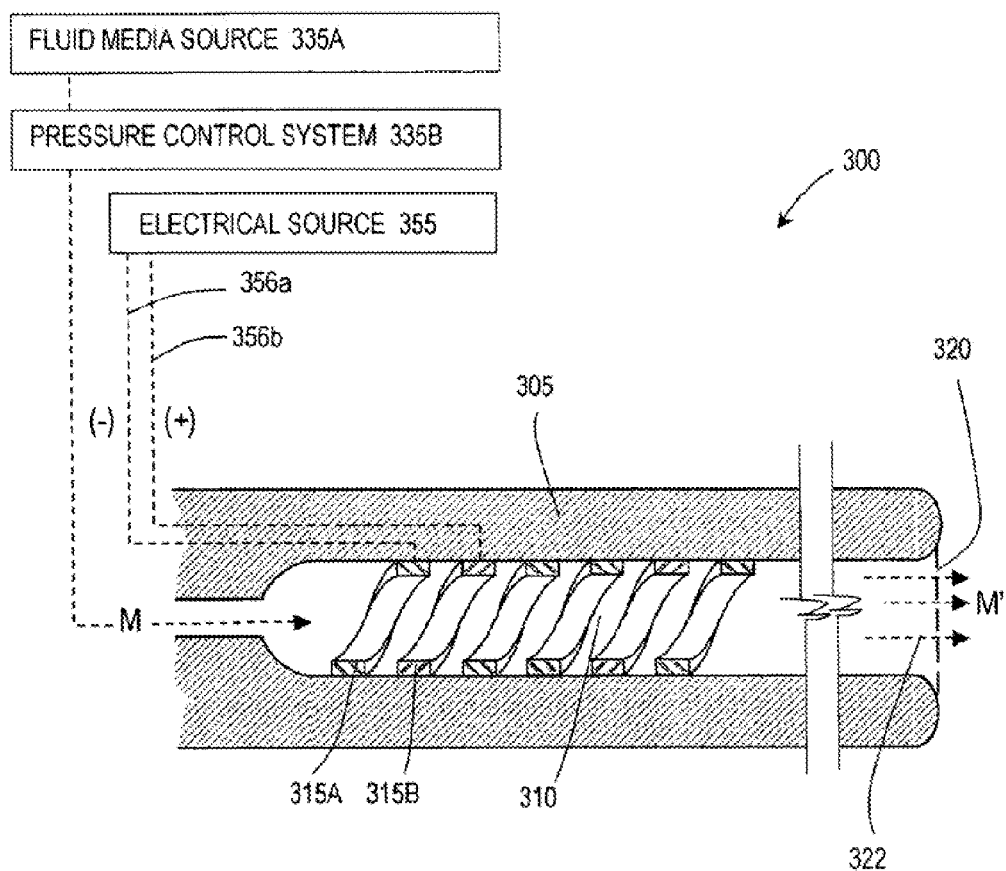
FIG. 10 is a schematic sectional view of an alternative working end with a helical electrode arrangement in the interior chamber.
Figure 11:
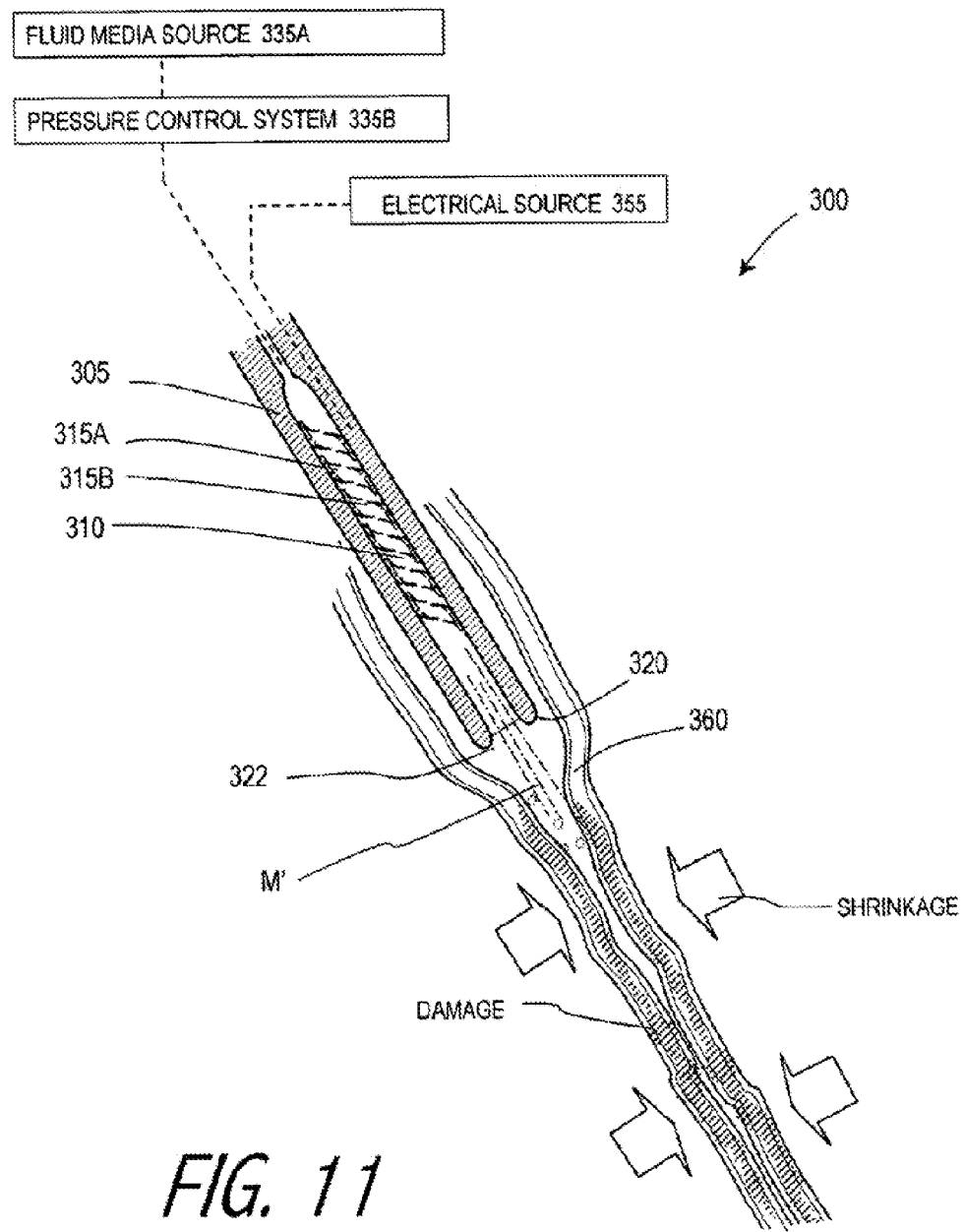
FIG. 11 illustrates a method of the invention in treating a blood vessel disorder with the device of FIG. 10.

Now referring to FIGS. 10 and 11, another embodiment of instrument working end 300 is shown in schematic sectional view. The previous devices were shown and optimized for having a working surface that engages tissue, and for controlling and limiting thermal effects in engaged tissue. In the embodiment of FIG. 10, the working end is adapted for controlled application of energy by means of phase change energy release in an endovascular application, or in media within or about other body lumens, ducts and the like.

FIG. 10 illustrates the working end 300 of a member or catheter body 305 that is dimensioned for introduction into a patient's vasculature or other body lumen. The diameter of body 305 can range from about 1 Fr. to 6 Fr. or more. The working end 300 typically is carried at the distal end of a flexible catheter but may also be carried at the distal end of a more rigid introducer member. In a rigid member, the working end also can be sharp for penetrating into any soft tissue (e.g. a fibroid, breast lesion or other organ such as a prostate) or into the lumen of a vessel.

The working end 300 of FIG. 10 has an interior chamber 310 again in communication with fluid media inflow source 335A and pressure control system 335B. The interior chamber 310 carries opposing polarity electrodes 315A and 315B as thermal energy emitters. The distal terminus or working surface 320 of the catheter has media entrance port 322 therein. In this embodiment, the electrodes 315A and 315B are spaced apart, indicated with (+) and (−) polarities coupled to electrical source 355, and are of a flexible material and configured in an intertwined helical configuration to provide a substantially large surface area for exposure to inflowing fluid media M. The electrodes can extend axially from about 1 mm to 50 mm and are spaced well inward, for example from 1 mm to 100 mm from the distal working surface 320. This type of electrode arrangement will enhance energy delivery to the liquid media M to allow effective continuous vaporization thereof. The lumen or chamber portion between electrodes 315A and 315B allows for focused energy application to create the desired energy density in the inflowing media M to cause its immediate vaporization. The vapor is then propagated from the working surface 320 via port 322 to interact with the endoluminal media. It should be appreciated that the instrument may have a plurality of media entrance ports 322 in the working surface, or additionally the radially outward surfaces of the catheter.

In the system embodiment of FIG. 10, the electrodes 315A and 315B are coupled to electrical source 355 by leads 356a and 356b. The working end 300 also is coupled to fluid media source 335A that carries pressurization means of any suitable type together with a pressure control system indicated at 335B.

In FIG. 11, the method of the invention is shown graphically wherein the distal end 300 is introduced into vasculature for the purpose of creating thermal effects in the vessel walls 360. In one targeted endovascular procedure, as depicted in FIG. 11, the objective is to apply controlled thermal energy to tissue to shrink and/or damage vessel walls to treat varicose veins. Most endothelial-lined structures of the body, such as blood vessel and other ducts, have substantially collagen cores for specific functional purposes. Intermolecular cross-links provide collagen connective tissue with unique physical properties such as high tensile strength and substantial elasticity. A well-recognized property of collagen relates to the shrinkage of collagen fibers when elevated in temperature to the range 60° to 80° C. Temperature elevation ruptures the collagen ultrastructural stabilizing cross-links, and results in immediate contraction in the fibers to about one-third of their original longitudinal dimension. At the same time, the caliber of the individual collagen fibers increases without changing the structural integrity of the connective tissue.

As represented in FIG. 11, the delivery of energy from the electrodes 315A and 315B to an inflow of liquid media M, such as any saline solution, will cause its instant vaporization and the expansion of the vapor (in addition to pressure from pressure source 335B) will cause high pressure gradients to propagate the heated vapor from port 322 to interact with endovascular media. The pressurized fluid media source 335A and pressure control subsystem 335B also can be adapted to create a pressure gradient, or enhance the pressure gradients caused by vapor expansion, to controllably eject the heated vapor from the working surface 320. As depicted in FIG. 11, the vaporized media M' deposits energy to the vessel walls in the vapor to liquid phase change energy release. The vaporized media is at about 100° C. as it crosses the interface between the working surface 320 and blood and will push the blood distally while at the same time causing the desired thermal effects in the vessel wall 360.

As shown in FIG. 11, the collagen in the vessel walls will shrink and/or denature (along with other proteins) to thereby collapse the vessel. This means of applying thermal energy to vessel walls can controllably shrink, collapse and occlude the vessel lumen to terminate blood flow therethrough, and offers substantial advantages over alternative procedures. Vein stripping is a much more invasive treatment. Rf closure of varicose veins is known in the art. Typically, a catheter device is moved to drag Rf electrodes along the vessel walls to apply Rf energy to damage the vessel walls by means of causing ohmic heating. Such Rf ohmic heating causes several undesirable effects, such as (i) creating high peak electrode temperatures (up to several hundred degrees C.) that can damage nerves extending along the vessel's exterior, (ii) causing non-uniform thermal effects about valves making vessel closure incomplete, and (iii) causing vessel perforations as the catheter working end is dragged along the vessel walls. In contrast, the energy delivery system of the invention utilizes the heat of a vapor media that cannot exceed about 100° C. (or slightly higher depending on pressure) to apply energy to the vessel walls. This method substantially prevents heat from being propagated heat outwardly by conduction—thus preventing damage to nerves. There is no possibility of causing ohmic heating in nerves, since a principal advantage of the invention is the application of therapeutic heat entirely without electrical current flow in tissue. Further, the vapor and its heat content can apply substantially uniform thermal effects about valves since the heat transfer mechanism is through a vapor that contacts all vessel wall surfaces—and is not an electrode that is dragged along the vessel wall. In one method of the invention, the vapor M' can be propagated from working end 300 while maintained in a single location. Thus, the system of the invention may not require the navigation of the catheter member 305 through tortuous vessels. Alternatively, the working end 300 may be translated along the lumen as energy is applied by means of vapor-to-liquid energy release.

Another advantage of the invention is that the system propagates a therapeutic vapor media M' from the working surface 320 that can be imaged using conventional ultrasound imaging systems. This will provide an advantage over other heat transfer mechanisms, such as ohmic heating, that cannot be directly imaged with ultrasound.

The working end 300 and its method of use as depicted in FIGS. 10-11 can apply therapeutic heat to blood vessel wall to treat chronic vascular insufficiency (CVI). In this disorder, venous valves are impaired or nonfunctional due in part to vessel swelling and distention proximate to the valves. The working end 300 as depicted in FIG. 10 can be positioned within the vessel to apply heat to the distended vessel wall portions to restore venous valve function. Intraoperative ultrasound can be used to image the procedure and energy-tissue interaction. Alternatively, MRI can be used to image the energy-tissue interaction.

Figure 12:
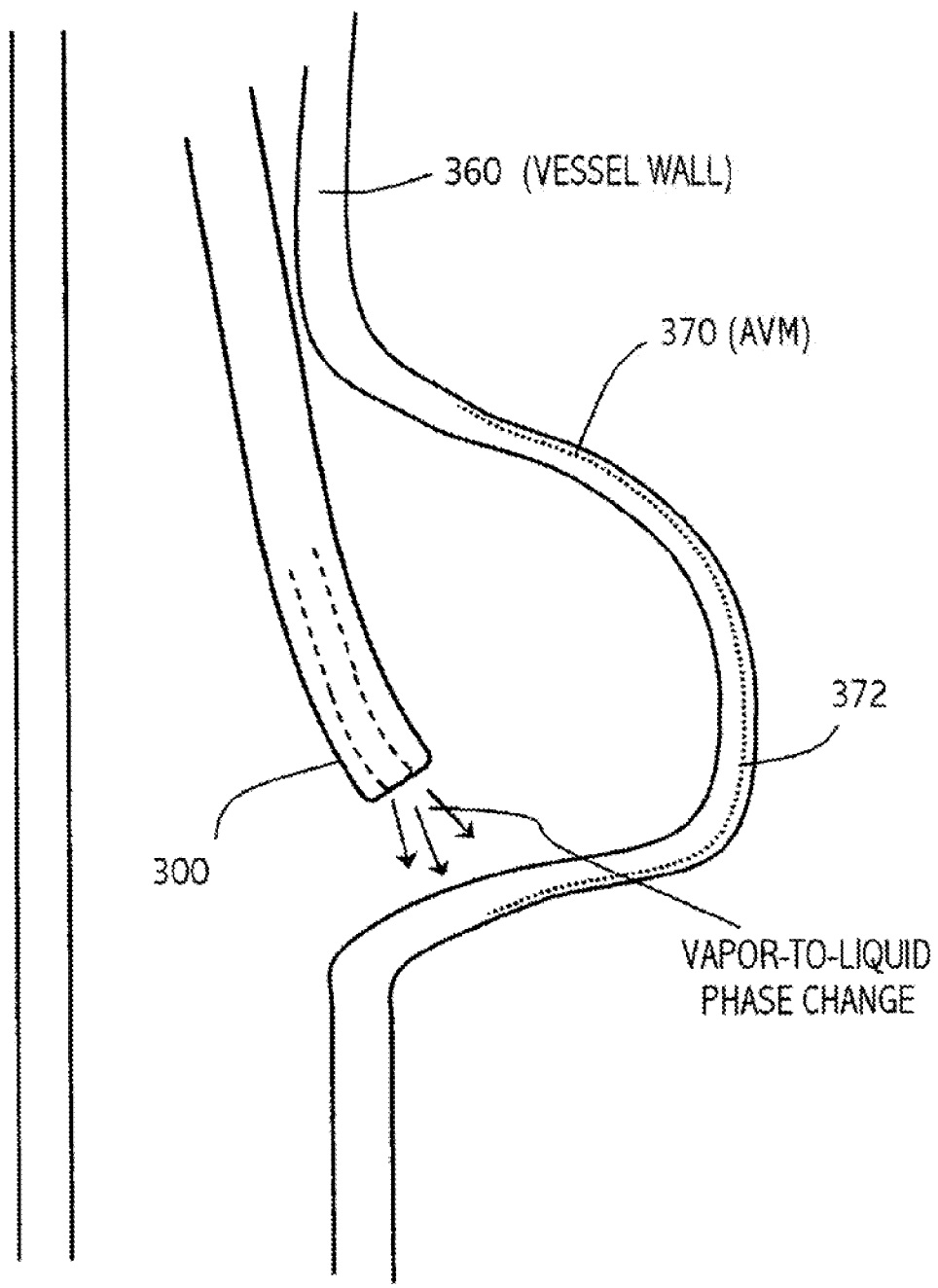
FIG. 12 illustrates an alternative method for treating an aneurysm.
Figure 13:
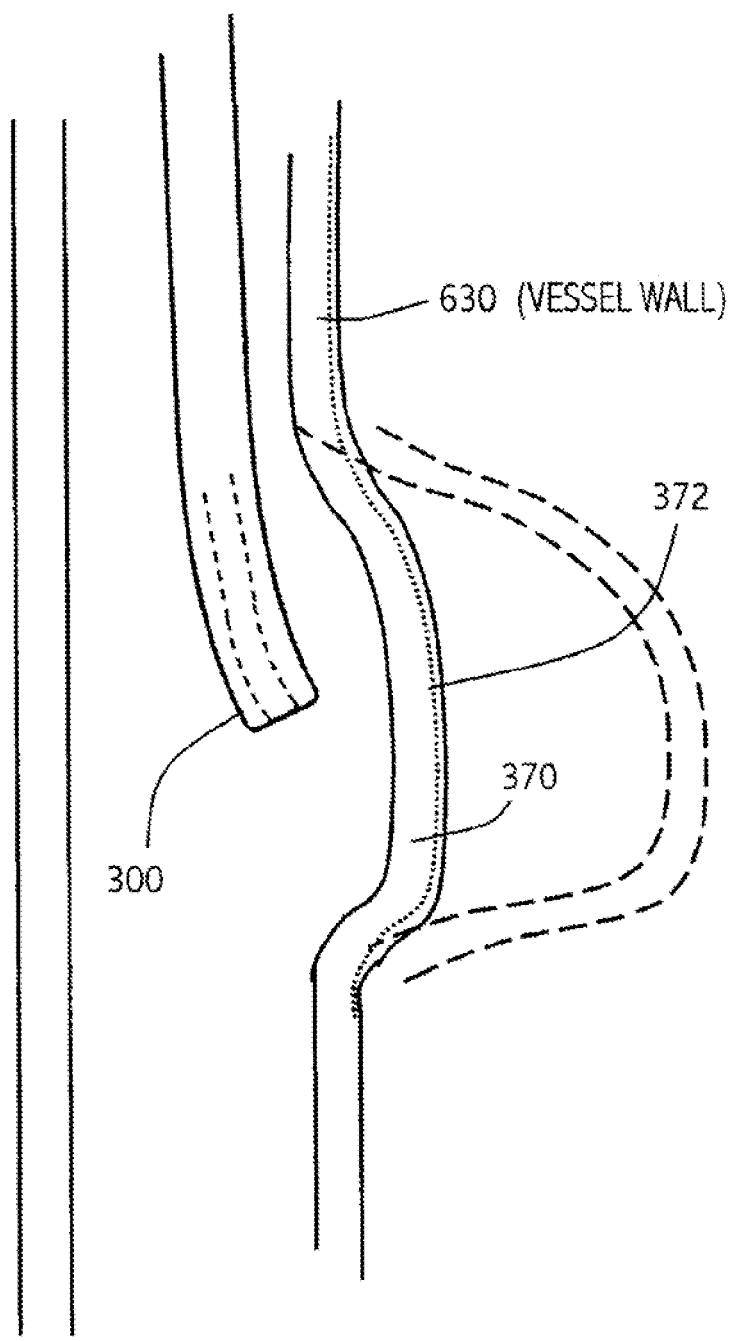
FIG. 13 illustrates the method of treating an aneurysm as in FIG. 12.

In a similar embodiment, a working end 300 as in FIG. 10 can be used to shrink any AVMs (arterial vascular malformations) such as an aneurysm. FIGS. 12-13 illustrate the use of working end 300 to shrink a wide-neck aneurysm 370. It has been found that the ejection of vapor media is reflected by fascia 372 of a blood vessel or other organ lining. Therefore, the shrinkage of the vessel wall occurs very rapidly without transfer of energy outside the vessel—as would occur in the application of mono-polar Rf energy to a vessel wall. The vessel wall of an AVM also thickens as it shrinks thus strengthening the wall, which contrast the method from packing the aneurysm with embolic materials which can further distend the vessel wall. The AVM treatment method further eliminates the use of embolic devices that can migrate. Further, the method can be used to treat wide-neck or "top-hat" aneurysm which cannot easily be treated with embolic materials.

In another method of the invention, the working end 300 as depicted in FIGS. 10-11 can be used to apply therapeutic heat to any duct, cavity, lumen or the like in the body to shrink, collapse or damage the anatomic walls or to fuse together and seal endothelial layers thereof. For example, the system and method can be used for tubal ligation in a treatment of fallopian tubes, or for closing microvasculature to terminate blood flow to vascularized diseased tissue, tumors and the like. Such embolic, vessel closure methods are used to starve cancerous tissues and fibroids from blood flow. Such vessel closure methods are also can be used to starve blood flow from alveoli in a lung volume reduction procedure for treating emphysema. The working end 300 can also be introduced within the patient's airways to directly deliver therapeutic heat to airways to cause their shrinkage or collapse to cause lung volume reduction.

The above working ends and methods have been described for use in endoluminal environments wherein the propagation of heated matter (vapor) can function optimally (i) within a fluid in the lumen, (ii) by displacing the fluid in the lumen, or (iii) by expanding a space within a collapsed lumen, duct, cavities separated by septae or the like. It should be appreciated that the systems and methods of the invention also can be used to apply energy directly to the interior of soft tissue volumes, for example to kill tumors. The heat vapor will propagate within extracellular spaces to thereby cause therapeutic heating for the purpose of creating lesions or killing tissue.

Figure 14:
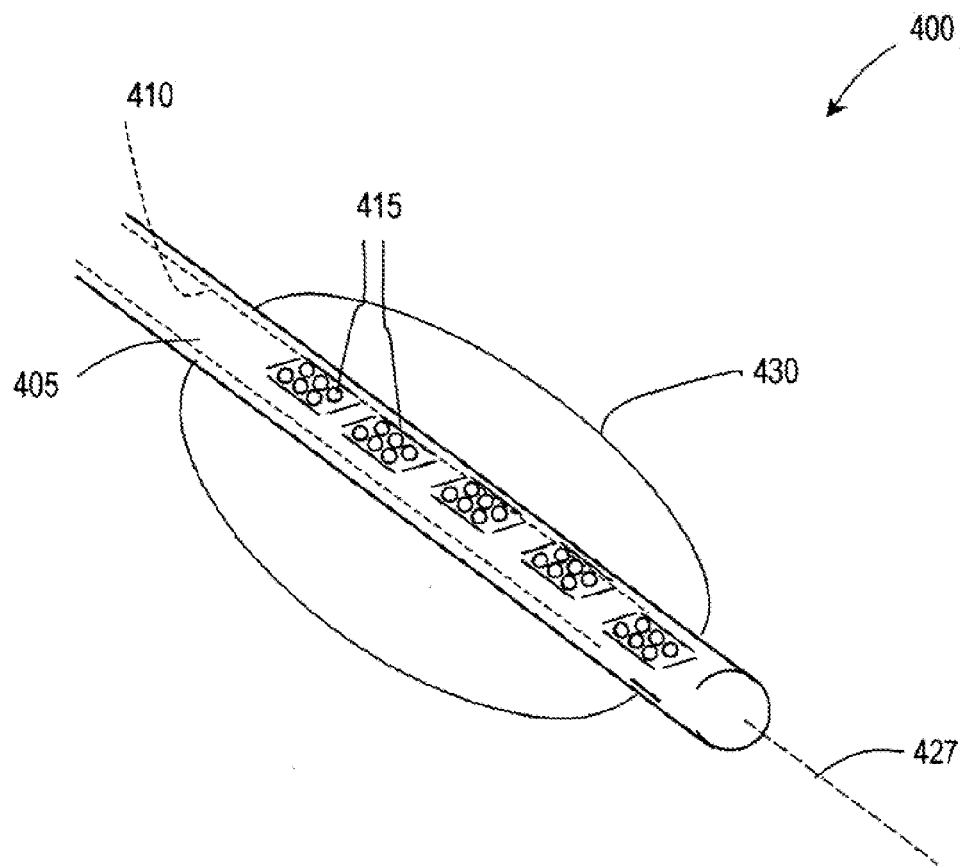
FIG. 14 is a perspective view of an alternative working end of a Type "B" embodiment with a plurality of microchanneled structures in a catheter.

2. Type "B" Thermotherapy Device. FIG. 14 illustrates an alternative working end 400 carried by an elongate flexible catheter body 405 of the type used in interventional cardiology. The working end 400 carries at least one microchannel structure 415 in working surface 420 as described above or applying energy by pressing surface 420 against targeted tissue. FIG. 14 depicts a plurality of microchannel bodies or structures 415 in the sidewall of a catheter working end to allow for flexibility, with the catheter body 405 being from 1.0 to 2.0 mm in diameter (not limiting). The microchannel structure is oriented so that vapor media M' is ejected substantially transverse to the axis 427 of the catheter. The targeted tissue T may be veins, myocardium or other cardiac tissue in which it is desirable to create a linear transmural lesion or ablation to alter electrical signal transmission in a treatment for atrial fibrillation as is known in the art. As shown in FIG. 14, the working end 400 is configured with a balloon 430 as is known in the art for positioning the working end in a treatment location. It is believed that the method of the invention can create the desired elongate linear thermal effect in the targeted tissue with greater control over (i) the lateral margins of the treatment path, and (ii) the depth of treatment, when compared to prior art radiofrequency devices that deliver Rf energy that courses through the tissue in an unpredictable manner.

Figure 15:
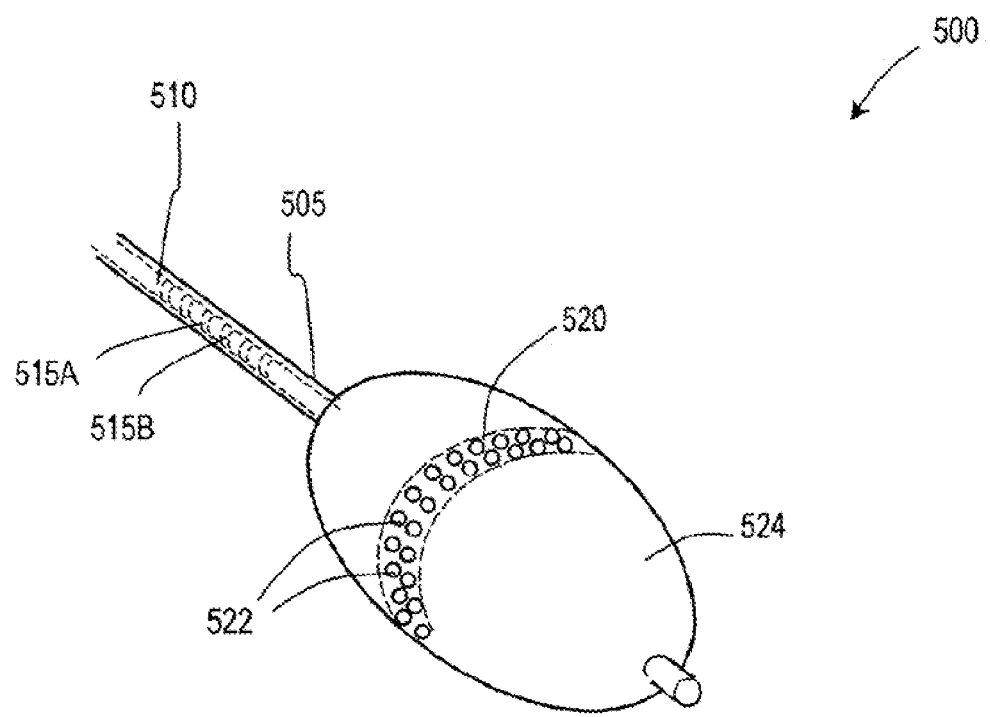
FIG. 15 is a perspective view of an alternative working end with apertures in the surface of an expandable structure.
Figure 16:
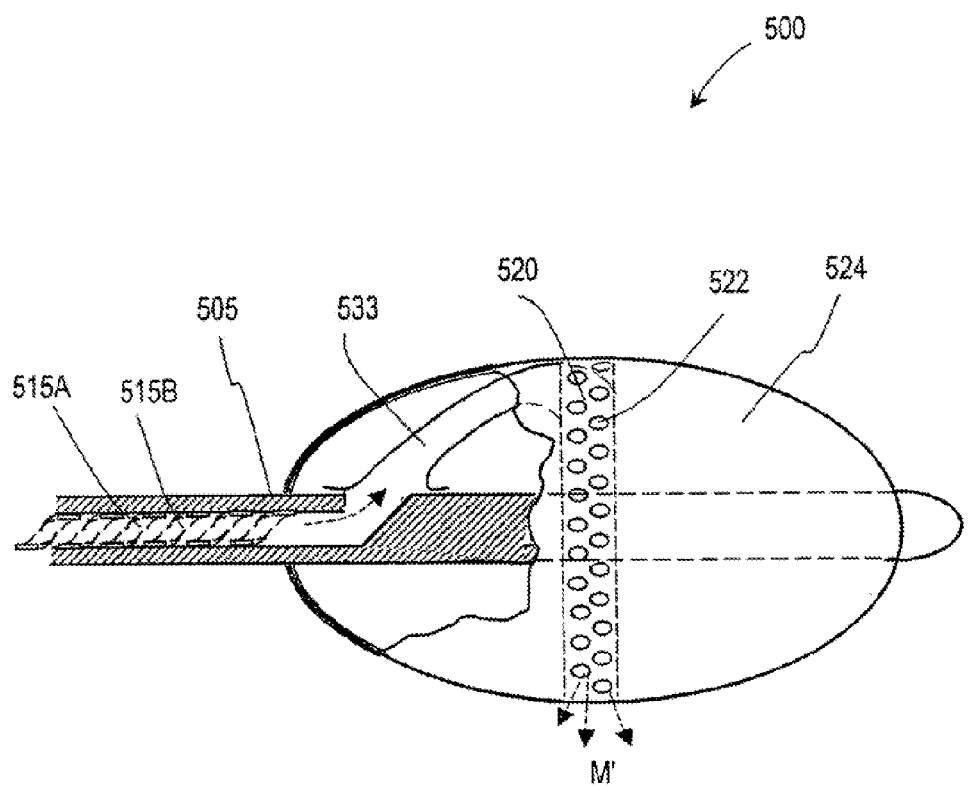
FIG. 16 is a cut-away view of the working end of a FIG. 15.

FIGS. 15 and 16 illustrate another embodiment of working end 500 for an endoluminal thermotherapy wherein the catheter body 505 carries interior chamber 510 and cooperating electrodes 515A and 515B (or a microchannel structure as in FIG. 8) for applying energy to inflowing liquid media M to cause it change in phase to vapor media M'. In this embodiment, the tissue-engaging surface 520 and outflow ports 522 are about the exterior of an expandable structure 524 that is distal to the interior chamber 510 and electrodes 515A and 515B. The interior chamber is coupled to the channel 525 by a flexible film lumen portion indicated at 533 in FIG. 16. The expandable structure 524 expands radially outward from the catheter axis to provide a linear, circumferential lesion. The outflow ports 522 are in the channel 525 formed in a temperature resistant laminate of the thin film polymer layers. The expandable structure can be an expandable balloon or mechanically actuated structure. In one embodiment as in FIGS. 15-16, the expandable structure 524 is a balloon of a non-distensible polymer that is expanded by a liquid that can be cooled to assist in controlled application of energy to tissue along the line of the outflow ports 522. The balloon inflation lumen is not shown for convenience. The working surface 520 can create circumferential lesions in pulmonary veins that are needed in treating atrial fibrillation—the most common form of cardiac arrhythmia (abnormal electrical signals in the heart), affecting more than 5 million people worldwide. It should be appreciated that the flex structure can be con configured about a deflectable working end of an instrument to engage about the exterior of a pulmonary vein for a pulmonary vein ablation treatment as is known in the art. The method of fabricating the flexible structure 524 is described below.

Figure 17:
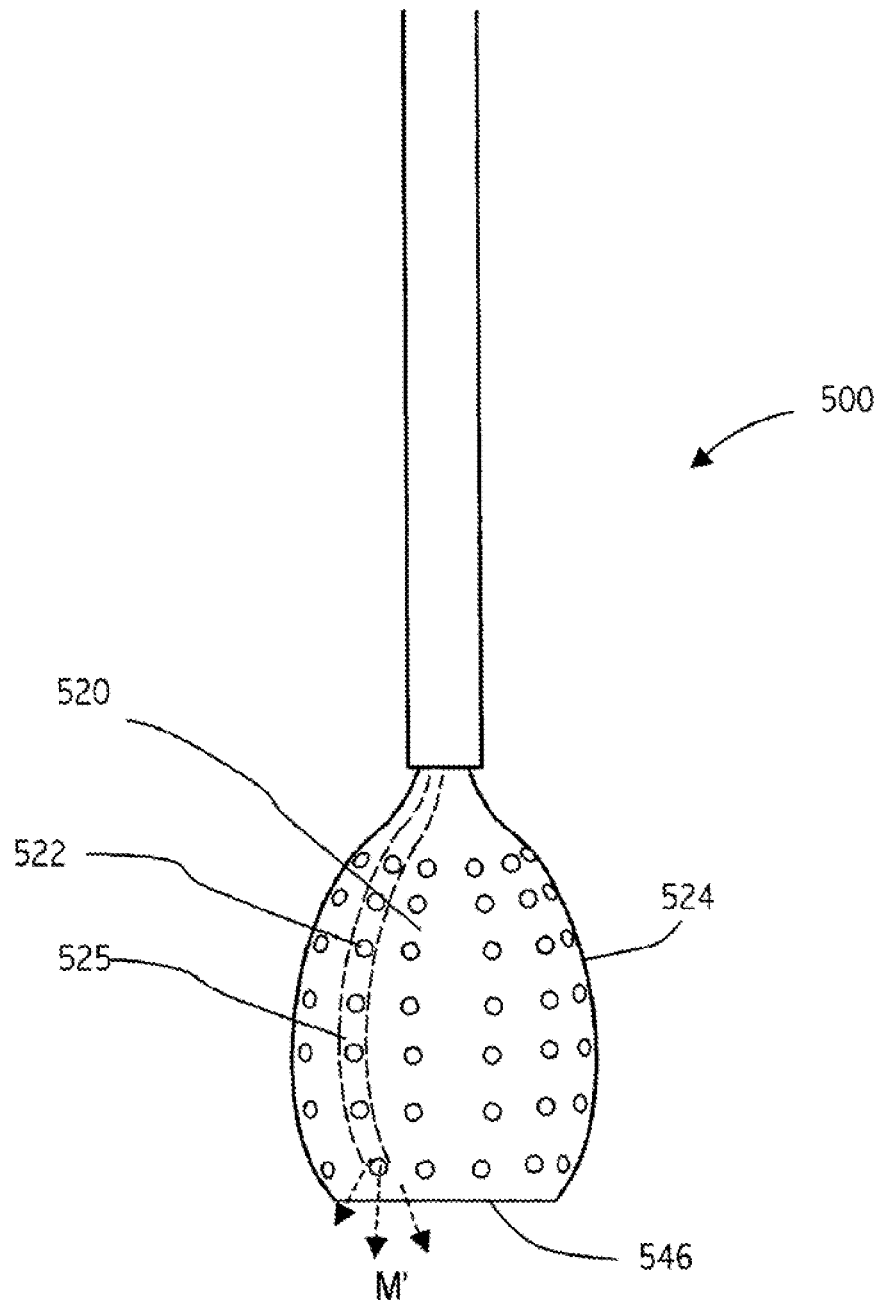
FIG. 17 is a plan view of an alternative working end with apertures in the surface of a thin-film structure for engaging and collapsing in a body cavity.

FIG. 17 illustrates another exemplary embodiment 500 with working surface 520 and inflow ports 522. This alternative flexible structure 524 is preformed for engaging the interior geometry of a lumen or cavity in any body structure or organ. The flexible structure 524 can be an expandable balloon, a structure expandable by any mechanical mechanism or a shape memory alloy or shape memory polymer, or an open web structure, for example expanded by gel infusion. Or the device as in FIG. 17 can have an open end 546 and be expanded to net shape of the structure as vapor media in pushed into channels 525 under pressure. The flexible structure 524 has a plurality if channels 525 with openings 522 therein to allow the exit a vapor phase media M' that is delivered under controlled pressure to the channels. The embodiment of FIG. 17, for example, can be used for applying energy to the wall 360 of an aneurysm (cf. FIGS. 12-13). It should be appreciated that the flexible structure 524 also can take form of a highly elongate sleeve with perforations therein (not shown) for treating varicose veins. The flexible sleeve structure 524 would be inserted along the targeted length of the vein, and the openings in the sleeve would diffuse the delivery of vapor into all surfaces of the vessel. The ports 522 can be directed away from perforator vessels. Such a sleeve 524 can be releasable from the instrument and of a bioasorbable polymer. The sleeve can be left in place in the blood vessel. Such a device would be capable of directing high pressure flows in the desired direction and expand under inflow pressures of vapor media M'—and then collapse under the force of vessel shrinkage. The device would prevent thermal migration into perforators that extend between surface and deep vein systems.

Figure 18A:
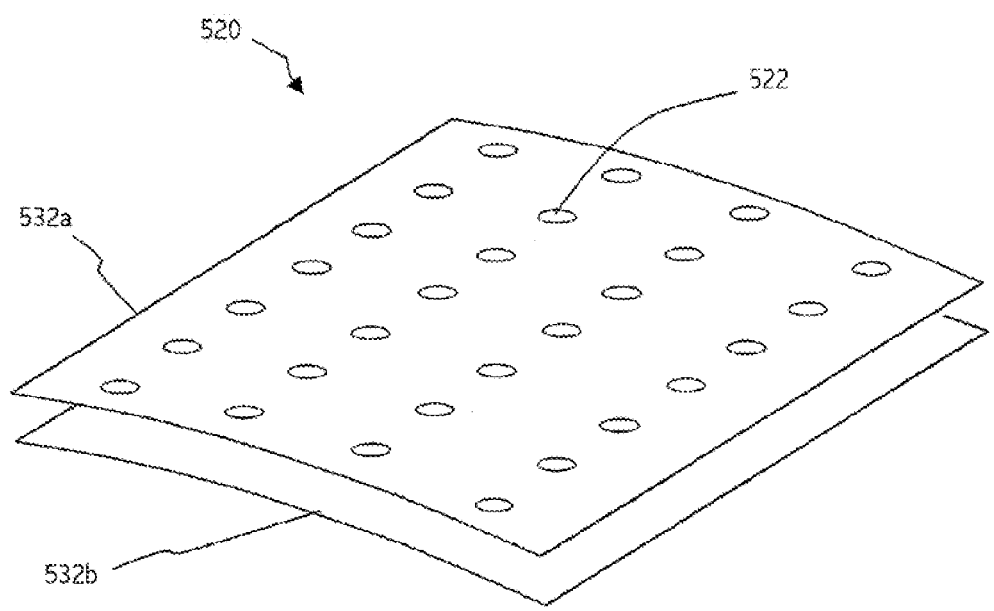
FIG. 18A is a view of a method of fabricating the thin-film structure of FIG. 17.
Figure 18B:
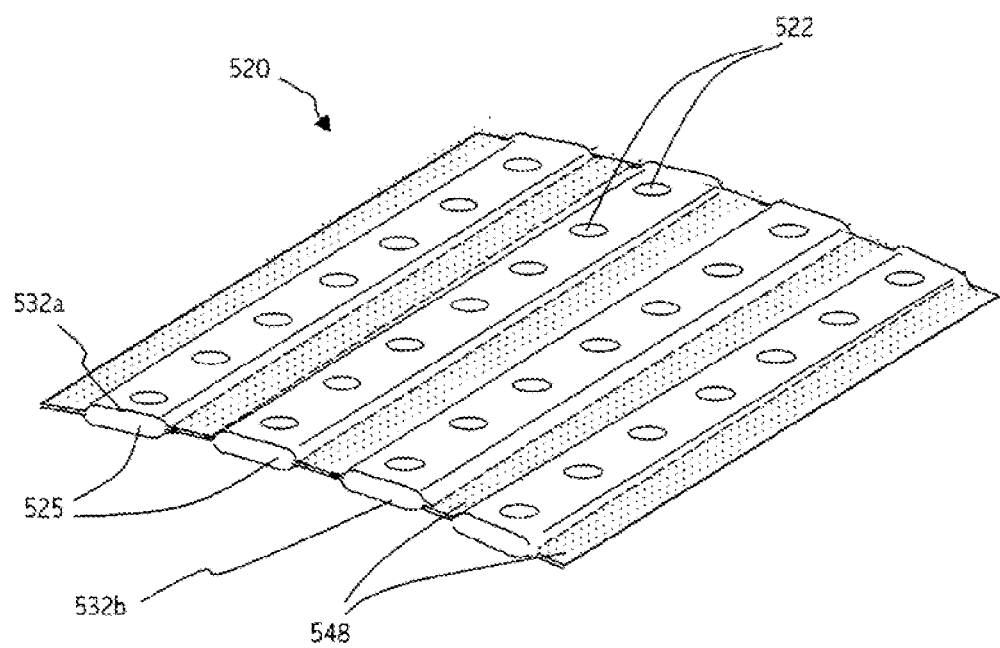
FIG. 18B is another view of a method of fabricating the thin-film structure of FIG. 17.

FIGS. 18A and 18B illustrate the method of making the expandable structure and working surface 520 of the device of FIG. 17. Thin film materials 532a and 532b of a temperature resistant material can be used and bonded (thermally or with adhesives etc.) along weld lines 548 to create channels 525. The openings or ports 522 can be laser cut or created in cooperating patterns by any suitable means. The ports and channel dimensions can have cross-sections (or branches) in controlled varied dimensions or shapes for causing a uniform outflow of vapor phase media M' along the length of an elongate channel.

Figure 19:
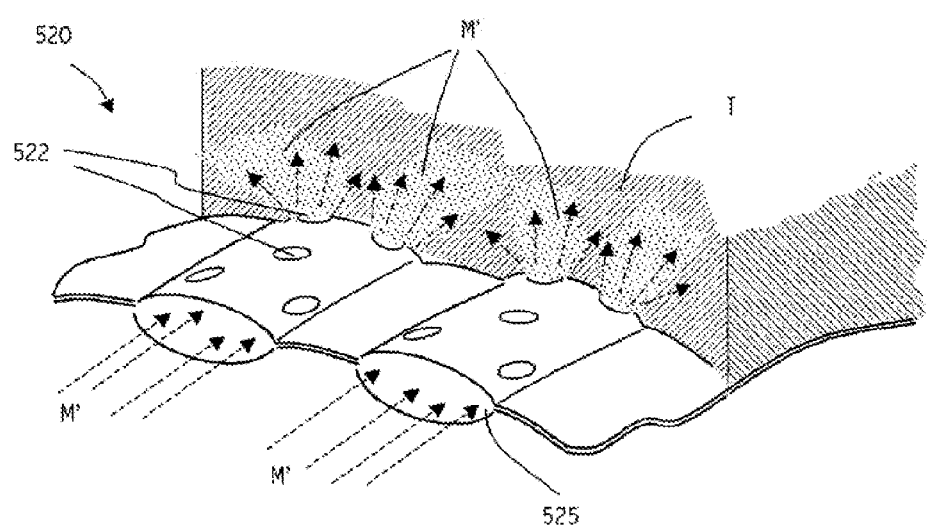
FIG. 19 illustrates the thermotherapy method utilizing the thin-film structure of FIG. 17.

FIG. 19 illustrates an exemplary cut-away view of a working surface 520 and channels 525 and further illustrating the release of the heat of vaporization to the engaged tissue in the vapor-to-liquid phase transition as vapor media exits ports 522. The tissue can be any interior of any body organ, such as a patient's uterus in an endometrial ablation treatment.

Figure 20A:
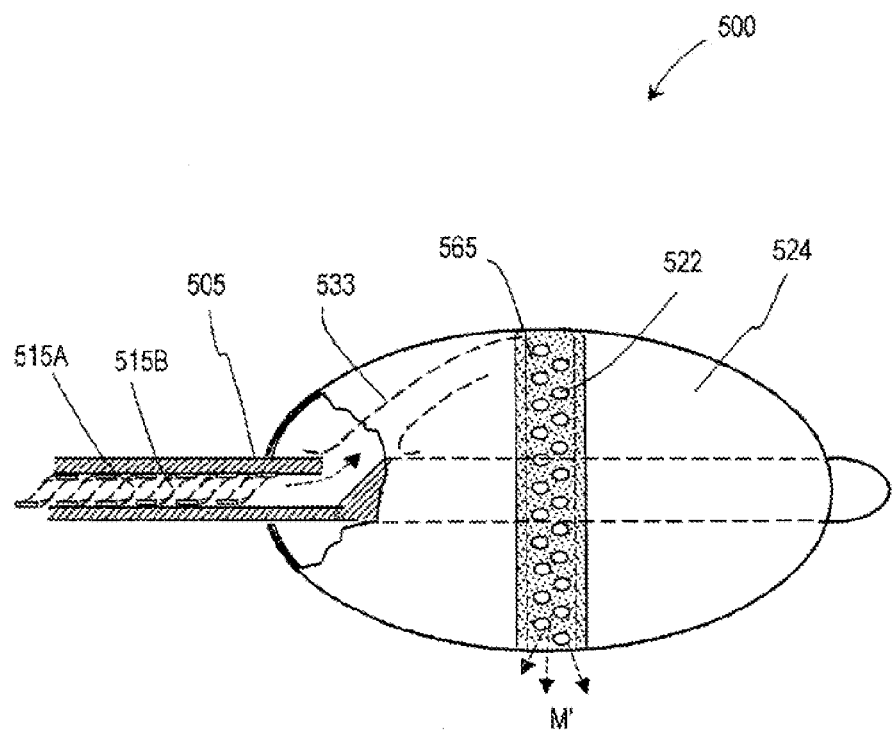
FIG. 20A is a plan view of an alternative working end.
Figure 20B:
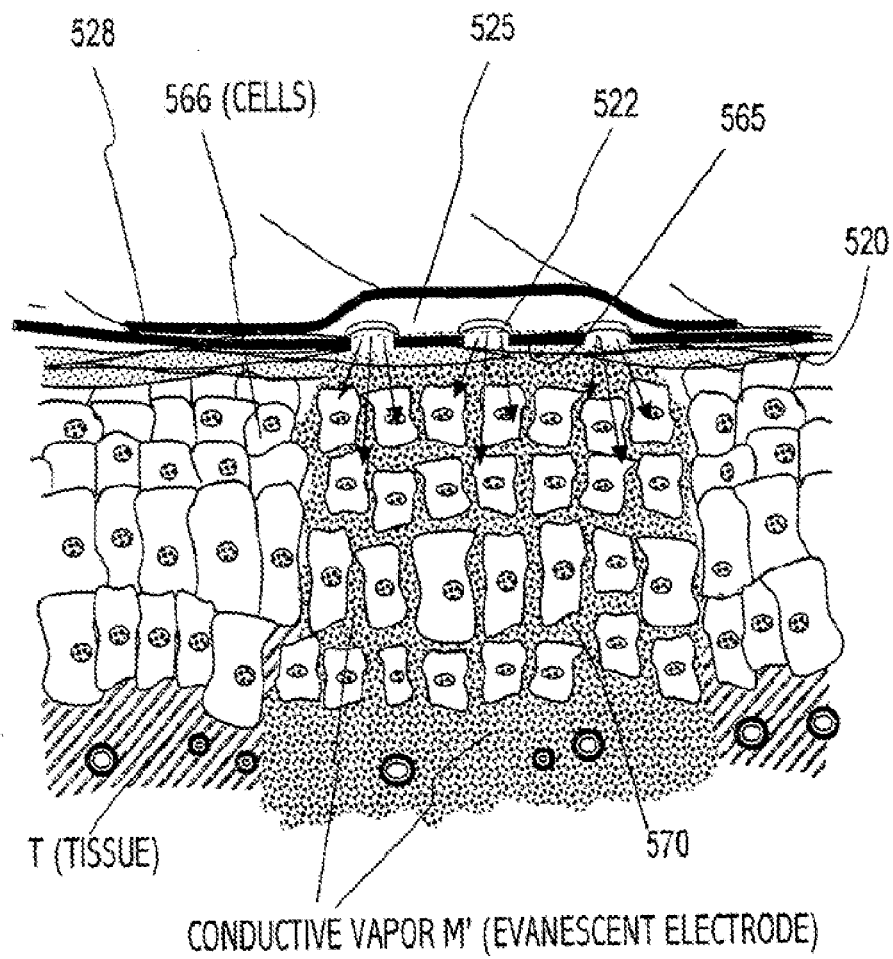
FIG. 20B depicts a greatly enlarged schematic view of the thin-film structure of FIG. 20A showing electrical energy delivery to conductive vapor media injected deep into a soft tissue volume.

FIGS. 20A-20B illustrate an enhanced means of energy delivery to tissue from an expandable flex structure 524 similar to that depicted in FIGS. 15 and 19. The expandable structure 524 in FIG. 20A carries an additional conductive surface (electrode) layer indicated at 565 about the surface of the structure proximate the inflow ports 522. It should be appreciated that the conductive surface 565 can be provided in any working surface (or interior of any working surface) in the various embodiments described above. The conductive surface 565 is coupled to an electrical source and a controller, but is adapted to function independently from, or in cooperation with, the electrical discharges that convert the liquid media to vapor media. Electrical energy delivery to surface electrode 565 can be intermittent a high Hz rate of energy delivery to the vaporizing electrodes 515A and 515B, or out of phase, for example. FIG. 20B is a schematic view of the method of the invention, showing a small portion of expandable structure 524 and channel 525 pressed against tissue. Vapor media M' is ejected under high pressure from ports 522 deep into tissue as depicted above in FIG. 19. The media is a high saline content solution that is vaporized in the instrument working end as described above and injected under high pressure into soft tissue T. It has been found that such vapor injection migrates in extracellular spaces between cells 566. The vapor media M' is also conductive (as it consists of a transient ionized plasma) as it extends very deep into soft tissue under the high pressure propagation before it condenses and delivers energy to tissue in the phase change release. At the time that the vapor media M' is with in the intracellular spaces 570, it can serve as a gas electrode (or evanescent electrode) that can conduct high voltage in cooperation with a ground pad until the vapor plume collapses. The method of the invention thus comprises applying voltage to the gas electrode (from conductive surface 565) within the extracellular spaces or deep tissue spaces to apply ablative energy to the tissue T. Thus, the phase transition energy release can be enhanced by energy delivery via the evanescent electrode means. This form of enhanced energy delivery will be uniform about the surface of the—in effect—gas electrode that evanesces (vanishes) leaving only dispersed water drop-lets. By these means, thermal ablation or shrinkage of vessel lumens or soft tissues can be accomplished very rapidly, under ultrasound visualization. In soft tissue applications, it has been found that the vapor media can be introduced deep into tissue volumes through extracellular fluid spaces to apply high energy densities throughout the targeted tissue volume. In effect, the evanescent electrode for micro-second or longer time scale extends throughout the tissue—not just contacting the tissue surface as is mono-polar or bi-polar Rf. While the method of applying electrical energy to the conductive plasma or vapor is shown in soft tissue in FIG. 20B, the method applies equally to use in body lumens as in the treatment of varicose veins as in FIG. 11.

Figure 21:
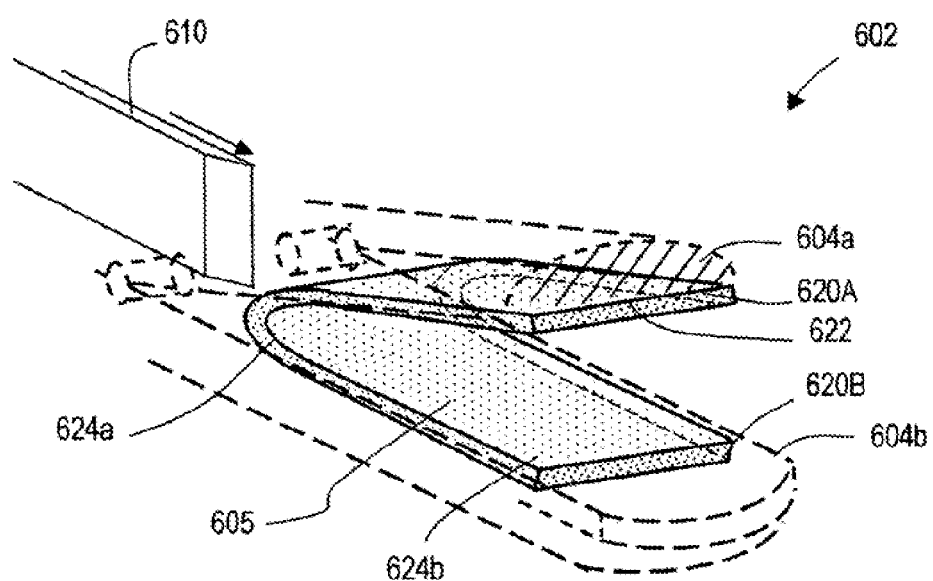
FIG. 21 is a schematic view of an alternative instrument working end for sealing/transecting tissue with a jaw structure that carries a releasable weldable polymer clip of a bioresorbable composition.

FIG. 21 illustrates an alternative working end 600 that comprises an openable-closeable jaw structure 602 with first and second jaws 604a and 604b that are moveable between a first open position and a second closed position to compress engaged tissue together with a releasable polymer clip-like element 605 carried within the jaws. The clip element 605 is adapted for providing sealing functionality in addition to the thermal sealing caused by energy delivery as described above. The sealed vessel also optionally can be transected with a blade 610 in the jaw structure 604 as in known in the art. In this working end, the jaw structure 602 carries a dematable weldable clip of a heat shrinkable polymer or a similar shape memory polymer. Preferably, the clip 605 is biodegradable. In FIG. 21, the surfaces of one or both jaws comprise working surfaces 620A and 620B that have ports 622 therein from which vapor media M' is ejected under high pressure as described above. In one embodiment, the jaws carry opposing bi-polar electrodes or another heating elements to fuse together the ends 624a and 624b of clip 605 about the tissue. The polymer clip 605 is substantially porous for allowing vapor media M' to propagate directly through the polymer to interact with, and further seal the tissue.

Figure 22A:
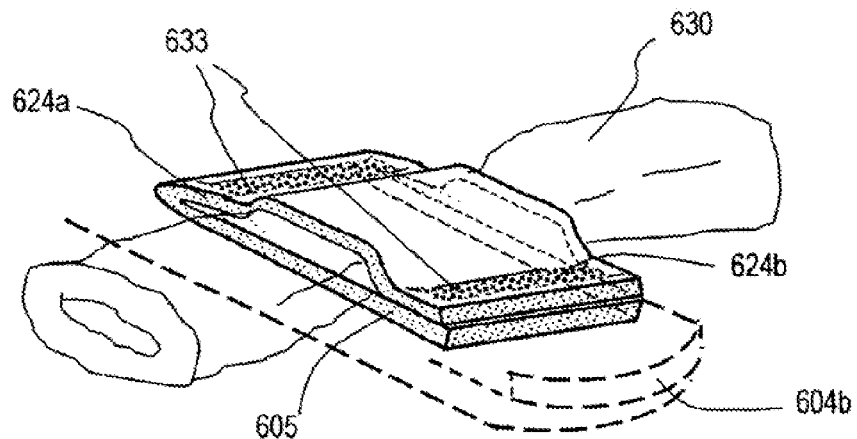
FIG. 22A is a schematic view of the working end and polymer clip of FIG. 21 depicting a first step in its method of use being clamped around a blood vessel and welded at the clip's free ends.
Figure 22B:
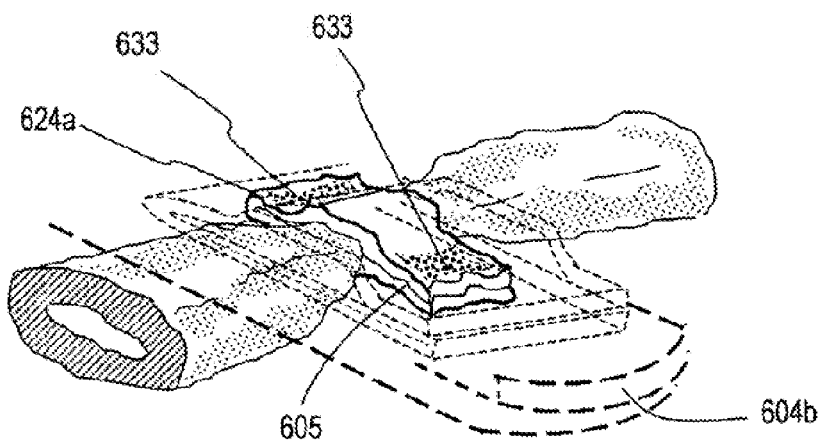
FIG. 22B is a schematic view of the polymer clip of FIG. 22A depicting the next step in its method of use wherein a vapor media is ejected through the polymer clip to seal the tissue and shrink the polymer.

FIG. 22A is a phantom view of jaw structure 602 (upper jaw not shown) clamping about a blood vessel 630 with the polymer clip 605 being compressed about the tissue. FIG. 22A also shows the ends 624a and 624b of clip 605 being welded at weld regions indicated at 633. FIG. 22B contemporaneously shows the method of shrinking the clip 620 wherein vapor media M' is ejected into the polymer clip from the jaws to seal the tissue while at the same time shrinking the biodegradable polymer within and about the captured tissue. The scope of the invention includes using the vapor media to melt and inject strands or webs of melted polymer through the captured tissue. Upon cooling, the polymer and tissue then form an integrated renatured composition for permanent sealing. It should be appreciated that the scope of the inventive clip extends to any form of energy delivery to shrink the clip, for example, Rf energy or laser energy. In one embodiment, the clip has projecting elements or barbs (not shown) to penetrate the tissue and any fascia to assist in vapor penetration into the captured tissue for more rapid delivery of thermal energy from the vapor to create a tissue seal. An instrument can be fabricated that carries a plurality of clips that can be advanced to the working end, much like a mechanical clip applier. The polymer clips also can carry imageable or radiopaque compositions.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A surgical thermally-mediated therapy for treating tissue comprising causing a controlled vapor-to-liquid phase state change of a selected media in a tissue site by causing a sufficient amount of energy to conduct through the selected media when contained within an instrument such that the selected media increases in volume causing pressurized ejection of the selected media from the instrument into the tissue site thereby applying thermal energy substantially equal to the heat of vaporization of the media to said tissue site causing the vapor media to propagate extracellularly in tissue when in a vapor state and allowing the media to undergo a vapor-to-liquid phase state change and release thermal energy to the tissue and further introducing the vapor media into an interior of a patient's body through an expandable member by engaging a body structure with the expandable member.

2. A surgical thermally-mediated therapy as in claim 1 wherein the heat of vaporization is in excess of about 500 calories per gram of the selected media.

3. A surgical thermally-mediated therapy as in claim 1 wherein the vapor-to-liquid phase state change is created within a patient's body after pressurized ejection of the selected media from at least one port of the instrument.

4. A surgical thermally-mediated therapy as in claim 1 wherein the vapor-to-liquid phase state change is created at a selected depth in tissue after pressurized ejection of the media from the instrument.

5. A surgical thermally-mediated therapy as in claim 1 wherein the vapor-to-liquid phase state change is created about a flexible working surface deployed in the interior of a body cavity or lumen.

6. A surgical thermally-mediated therapy as in claim 1 further comprising the step of controlling a parameter of the causing step selected from the class of parameters consisting of controlling the temperature of the vapor-to-liquid phase state change in the selected media, controlling the pressure of the media ejected from a working surface of the instrument, controlling the volume of the media being ejected from the working surface, and controlling the rate of delivery of the media volume being ejected from the working surface.

7. The method of claim 1 wherein the vapor media collapses in volume upon the vapor-to-liquid phase state change.

8. The method of claim 1 wherein the vapor-to-liquid phase state change applies thermal energy capable of modifying tissue.

9. The method of claim 1 wherein the vapor-to-liquid phase state change applies thermal energy capable of at least one of shrinking, sealing, welding and creating lesions in tissue.

10. The method of claim 1 wherein the vapor media has a temperature of at least 100° C.

11. The method of claim 1 including controlling at least one of the pressure of the vapor media, the volume of the vapor media, and the duration of a flow of the vapor media.

12. A method for thermally treating tissue comprising applying a first energy density to a fluid media when contained within a device such that the fluid media increases in volume causing a vapor media and subsequently providing a second energy density being lesser than the first energy density to maintain the vapor media; and expelling the vapor media from the device causing the vapor media to propagate extracellularly in tissue and allow the vapor media to undergo a vapor-to liquid phase state change and release thermal energy in the tissue.

13. A surgical thermally-mediated therapy for treating tissue comprising causing a controlled vapor-to-liquid phase state change of a selected media in a targeted tissue by modulating energy to apply a first amount of energy to the selected media when contained within an instrument such that the selected media increases in volume and transforms into a vapor media, and subsequently applying a second amount of energy being lesser than the first amount to maintain the vapor media; and controlling propagation of the vapor media using a pressure control system coupled to the instrument to cause pressurized ejection of the selected media from the instrument at a sufficiently high velocity to penetrate the targeted tissue and propagate within extracellular spaces of the targeted tissue to create a lesion in the targeted tissue.

* * * * *